(12) United States Patent
Yokota et al.

(10) Patent No.: US 7,708,027 B2
(45) Date of Patent: May 4, 2010

(54) CONNECTOR

(75) Inventors: Takayuki Yokota, Yamanashi (JP); Yoshinori Hishikawa, Yamanashi (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 568 days.

(21) Appl. No.: 11/628,723

(22) PCT Filed: Jun. 1, 2005

(86) PCT No.: PCT/JP2005/010077

§ 371 (c)(1), (2), (4) Date: Mar. 6, 2007

(87) PCT Pub. No.: WO2005/120630

PCT Pub. Date: Dec. 22, 2005

(65) Prior Publication Data

US 2007/0218745 A1 Sep. 20, 2007

(30) Foreign Application Priority Data

Jun. 7, 2004 (JP) .............................. 2004-168952

(51) Int. Cl.
*F16K 11/22* (2006.01)

(52) U.S. Cl. .................. 137/606; 251/149.3; 251/149.4; 251/149.6; 604/533

(58) Field of Classification Search ................. 137/605, 137/606; 251/149.4, 149.6, 149.9, 149.3; 604/533, 534, 537, 905

See application file for complete search history.

(56) References Cited

U.S. PATENT DOCUMENTS 5,620,426 A * 4/1997 Braithwaite .................. 604/533

| 5,685,866 | A | * | 11/1997 | Lopez ........................ 604/256 |
| 6,113,068 | A | | 9/2000 | Ryan |
| 6,299,131 | B1 | | 10/2001 | Ryan |
| 7,484,529 | B2 | * | 2/2009 | Yokota et al. ................ 137/606 |
| 2002/0024036 | A1 | * | 2/2002 | Rohrbough et al. ...... 251/149.1 |
| 2003/0120221 | A1 | * | 6/2003 | Vaillancourt ................ 604/905 |

FOREIGN PATENT DOCUMENTS

| JP | 3052138 U | 9/1998 |
| JP | 2002-526179 A | 8/2002 |
| JP | 2003-144546 A | 5/2003 |
| JP | 2003-325662 A | 11/2003 |

OTHER PUBLICATIONS

*International Search Report dated Jul. 12, 2005.

* cited by examiner

*Primary Examiner*—Stephen Hepperle
(74) *Attorney, Agent, or Firm*—Buchanan Ingersoll & Rooney PC

(57) ABSTRACT

A connector includes a housing having a first female-side connecting port, a liquid circulation space, and a male-side connecting section communicating with the liquid circulation space, a first valve disk made of elastic material and having a hollow section and a top slit formed in the top and received in the housing, a pin movably installed in the housing, and an urging section for urging the pin axially. In this connector, the top slit spreads and communication is established between a tube interior and the hollow section, and at the same time the top of the pin is pressed to cause the pin to move axially, enlarging the clearance between the hollow section and the pin, thereby establishing communication between the tube interior and the male-side connecting section interior successively through the top slit, the hollow section and the liquid circulation space.

18 Claims, 19 Drawing Sheets

(a)

(b)

(a)

(b)

CONNECTOR

TECHNICAL FIELD

The present invention relates to a connector provided with a valve mechanism for opening and closing a passage as a tube is connected thereto and detached therefrom.

BACKGROUND ART

In a medical circuit used for infusion, transfusion, nutritive dose or the like, connection and detachment of circuit parts may be carried out for sustained or temporary flows of a plurality of fluids such as medicines, blood, fluid diet, etc. It is well known that the circuit is fitted with a connector or connectors for this purpose.

A representative example of such connectors is a three-way cock. The three-way cock is composed of one male-type lure connector and two female-type lure connectors, and connection of circuit parts is carried out by fitting of the lure connectors. In this case, when a circuit part is detached, a portion serving as a fluid passage is exposed to the outside air, leading to poor resistance to contamination with bacteria. Particularly, the female-side connecting sections tend to be subjected repeatedly to connection and detachment, so that they are frequently exposed to the outside air.

In view of this problem, there has been a connector in which the female-side connecting port is equipped with a valve disk (valve element) for restraining the exposure to the outside air of the portion, serving as a fluid passage, of the female-side connecting port. In such a connector, the fluid passage is opened by piercing a vale body disk a needle or by inserting a male-type connector into a slitted valve disk; therefore, after the detachment of the needle or the male-type connector, the valve disk is again closed, whereby the fluid passage can be prevented from exposure to the outside air.

In these connectors, however, the valve disk is provided for the female-side connecting port on one side only. Therefore, when the male-type connector is detached from the female-side connecting port on the other side, the female-side connecting port would be exposed to the atmospheric air.

Besides, these connectors have drawbacks in that it is difficult to achieve good flow of the whole amount of a liquid medicine due to the presence of stagnation areas in the female-side connecting ports or that the presence of the stagnation areas would lead to an environment where propagation of bacteria is liable to occur. In addition, there has been the problem that while the interior of the connector is filled up with a fluid such as a liquid medicine prior to use thereof, it is difficult to deaerate the connector interior.

Furthermore, there has been the problem that the capacity of the connector is liable to change at the time of attaching or detaching a needle or a male-type connector to or from the female-side connecting port. For example, when the capacity of the connector is increased upon detachment of the male-type connector, blood is caused to flow backward from a blood vessel catheter connected to the connector into a catheter, which would cause closure of the blood vessel catheter.

DISCLOSURE OF INVENTION

It is an object of the present invention to provide a connector in which a passage is opened and closed assuredly attendant on the connection and detachment of a tube, the passage can be prevented from contamination, and stagnation of a liquid would not easily occur.

In order to attain the above object, according to the present invention, there is provided a connector including: a housing having a female-side connecting port to which a tube can be connected, a liquid circulation space through which a liquid is passed, and a tubular male-side connecting section communicating with the liquid circulation space;

a valve disk made of elastic material and having a hollow section and a top slit formed in the top and received in the housing;

a pin movably installed in the housing, with at least its top inserted in the hollow section; and an urging section for urging the pin axially, wherein the top slit is closed when the tube is not connected to the female-side connecting port; and when the tube is connected to the female-side connecting port, the tube presses the head of the valve disk to contract the valve disk, causing the top slit to spread, communication is thereby established between a tube interior and the hollow section, and at the same time the head of the pin is pressed to cause the pin to move axially, enlarging a clearance between the hollow section and the pin, thereby establishing communication between the tube interior and the male-side connecting section interior successively through the top slit, the hollow section and the liquid circulation space.

This ensures that the passage is assuredly opened and closed attendant on the connection and detachment of the tube, the passage can be prevented from contamination, and stagnation of a liquid can be prevented from occurring.

In addition, in the connector according to the present invention, preferably, the hollow section is substantially wholly filled up with the pin when the tube is not connected.

This prevents a liquid from stagnating in the hollow section of the valve disk.

Besides, in the connector according to the present invention, preferably, two sets of the valve disk, the pin and the urging section which share the liquid circulation space are provided.

This ensures that even when a liquid flows into the liquid circulation space from the side of the valve disk on one side or flows into the liquid circulation space from the side of the valve disk on the other side, the liquid will pass through the liquid circulation space, so that stagnation of the liquid can be prevented from occurring.

In addition, in the connector according to the present invention, preferably, the two sets of the valve disk, the pin and the urging section are so arranged that their center lines are located in correlation of skew lines.

This has the merit that the volume of the liquid circulation space can be made extremely small, as compared with the case where the center lines intersect each other on a plane.

Besides, in the connector according to the present invention, preferably, the pin has a tapered part gradually decreasing in outside diameter toward the top of the pin.

This ensures that the pin can be inserted into the hollow section of the valve disk easily and securely when the tube is detached (evulsed) from the female-side connecting section being in the condition where the tube is connected thereto.

In addition, in the connector according to the present invention, preferably, the pin is provided at the top thereof with a slant face inclined against the axial direction thereof and parallel to the length direction of the top slit.

This ensures that the top of the pin can easily enter into the top slit and, therefore, the top slit can be opened more assuredly when the tube is connected to the female-side connecting section.

Besides, in the connector according to the present invention, preferably, the top of the pin is so shaped as not to close the mouth of the tube when the tube is connected and the top of the pin abuts on the mouth of the tube.

This ensures that the top of the pin can easily enter into the top slit and, therefore, the top slit can be opened more assuredly when the tube is connected to the female-side connecting section.

In addition, in the connector according to the present invention, preferably, two said slant faces are provided, and the top of the pin is substantially triangular in longitudinal sectional shape.

This ensures that communication between the tube interior and the hollow section of the valve disk can be established through the opened top slit when the tube is connected to the female-side connecting section.

Besides, in the connector according to the present invention, preferably, the pin is provided with a recess in the top thereof.

This ensures that communication between the tube interior and the hollow section of the valve disk can be established through the opened top slit when the tube is connected to the female-side connecting section.

BEST MODE FOR CARRYING OUT THE INVENTION

Now, the connector according to the present invention will be described in detail below, based on preferred embodiment shown in the accompanying drawings.

First Embodiment

Figure 1:
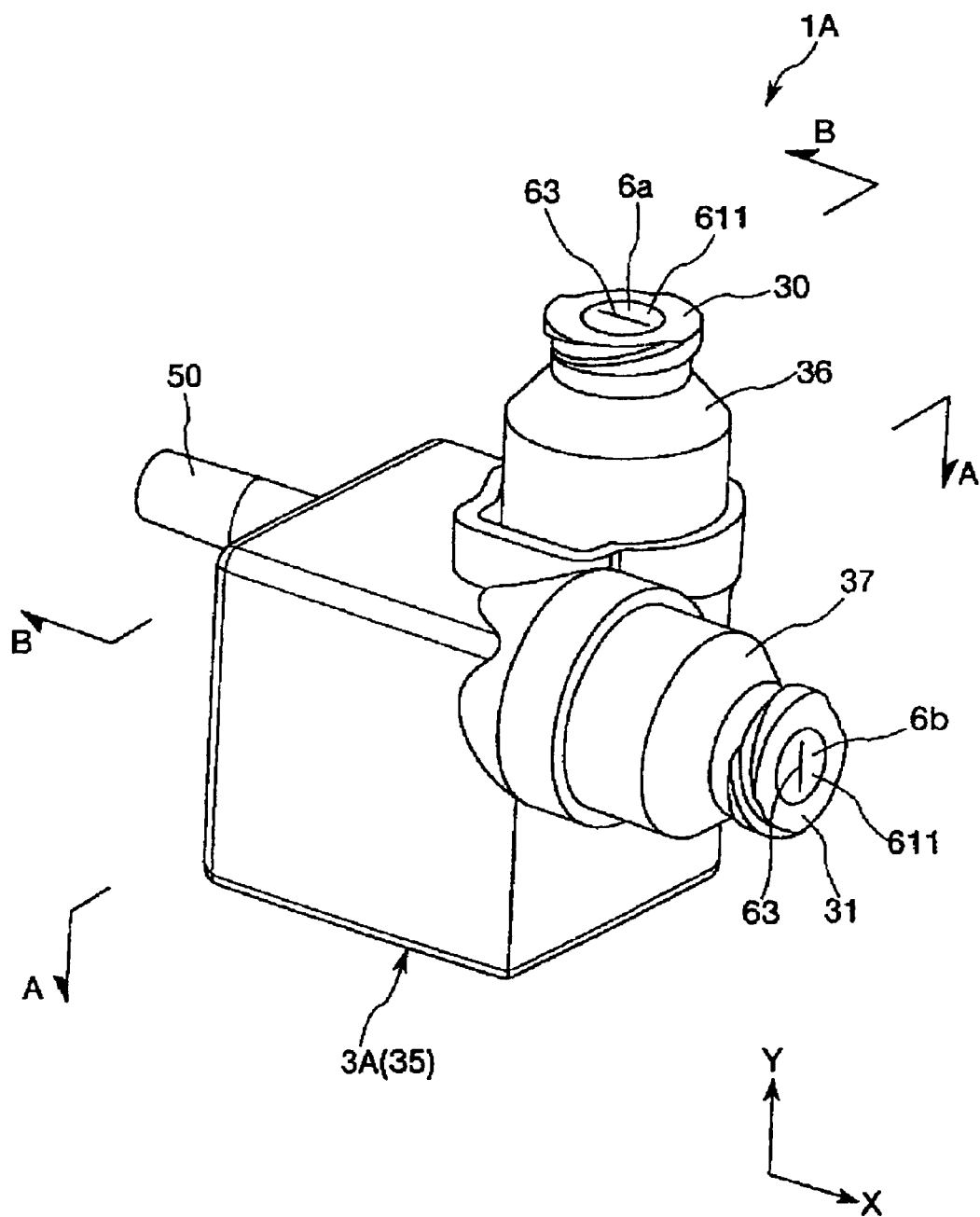
FIG. 1 is a perspective view showing a first embodiment of the connector according to the present invention.
Figure 2:
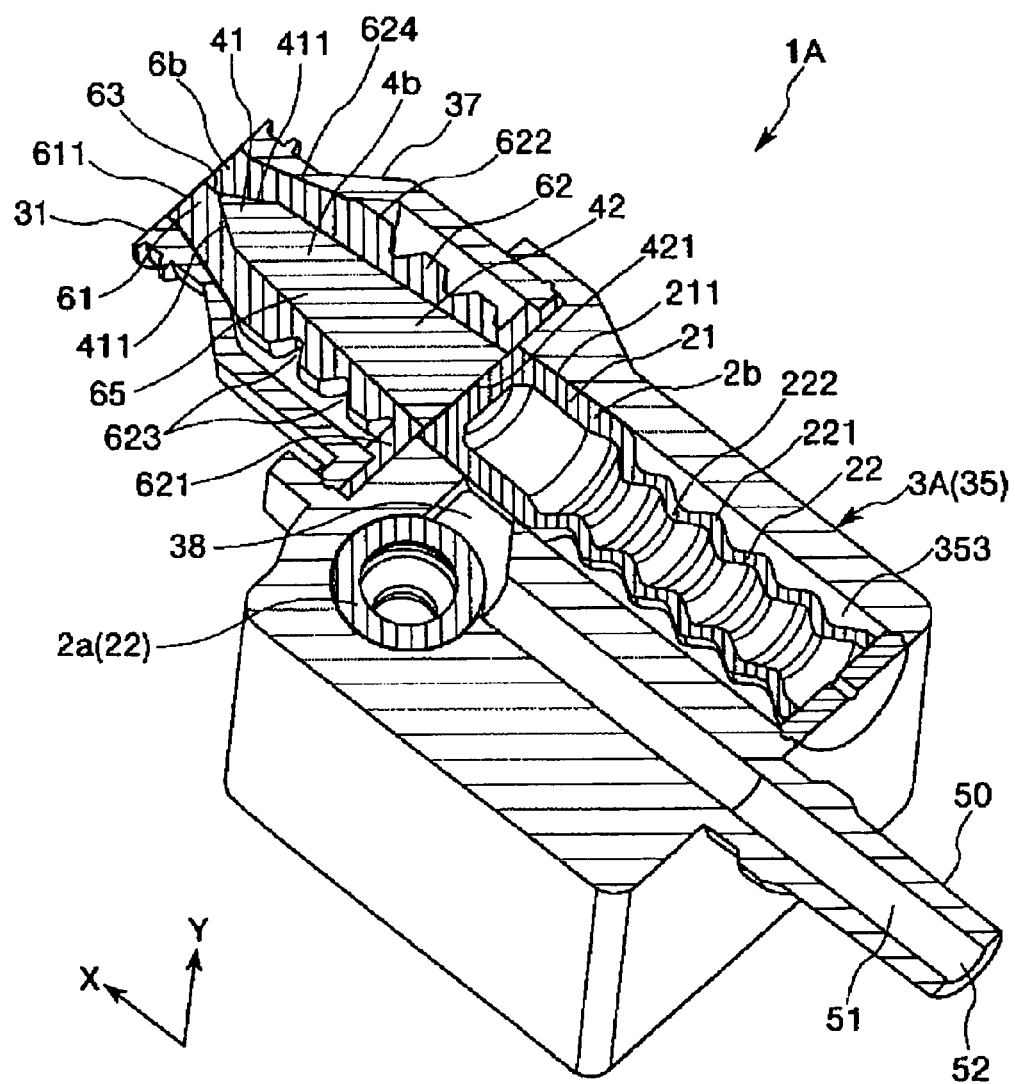
FIG. 2 is a sectional view taken along line A-A of FIG. 1.
Figure 3:
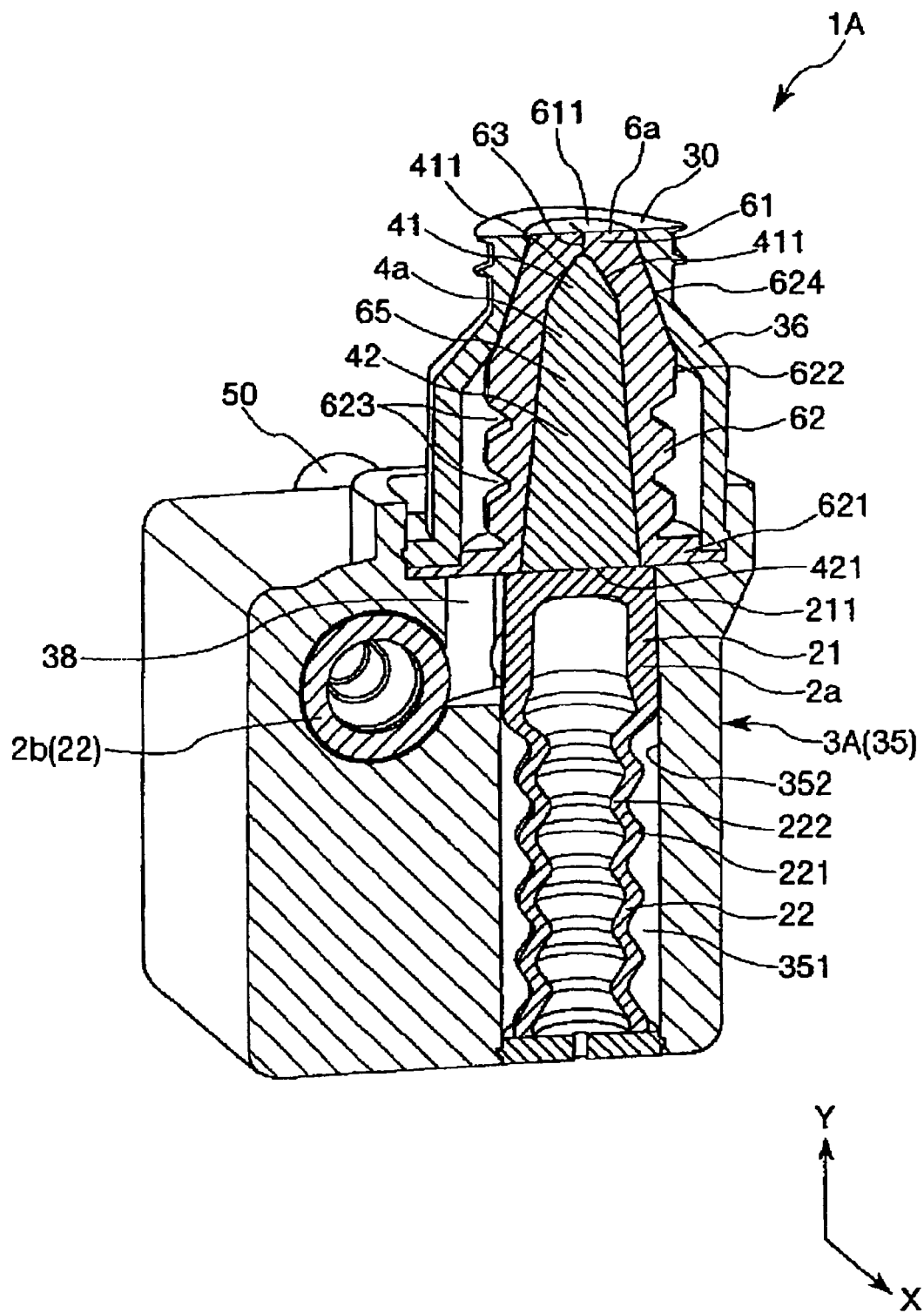
FIG. 3 is a sectional view taken along line B-B of FIG. 1.
Figure 4:
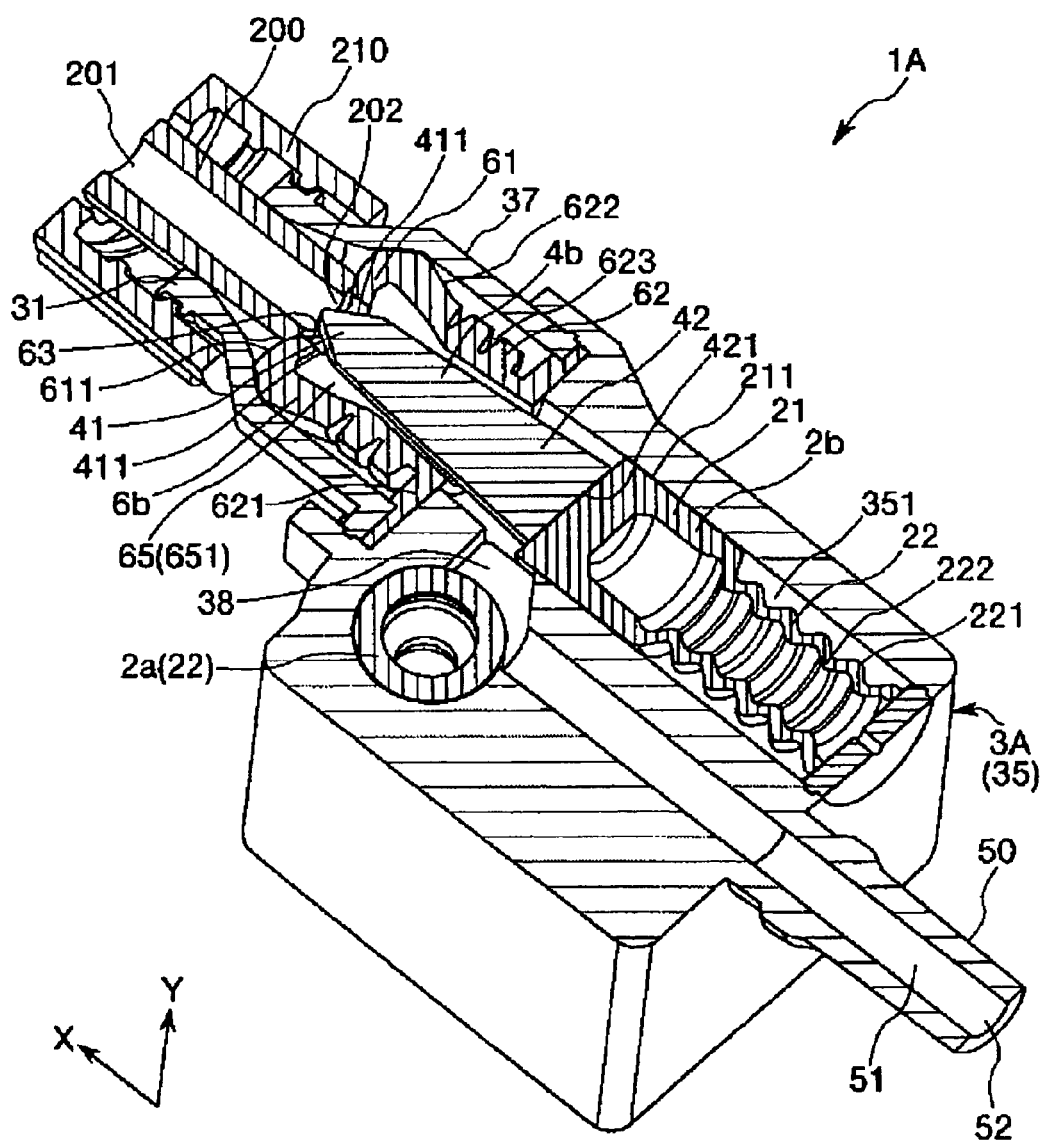
FIG. 4 is a sectional view taken along line A-A of FIG. 1 in the condition where a tube is connected to the connector.
Figure 5:
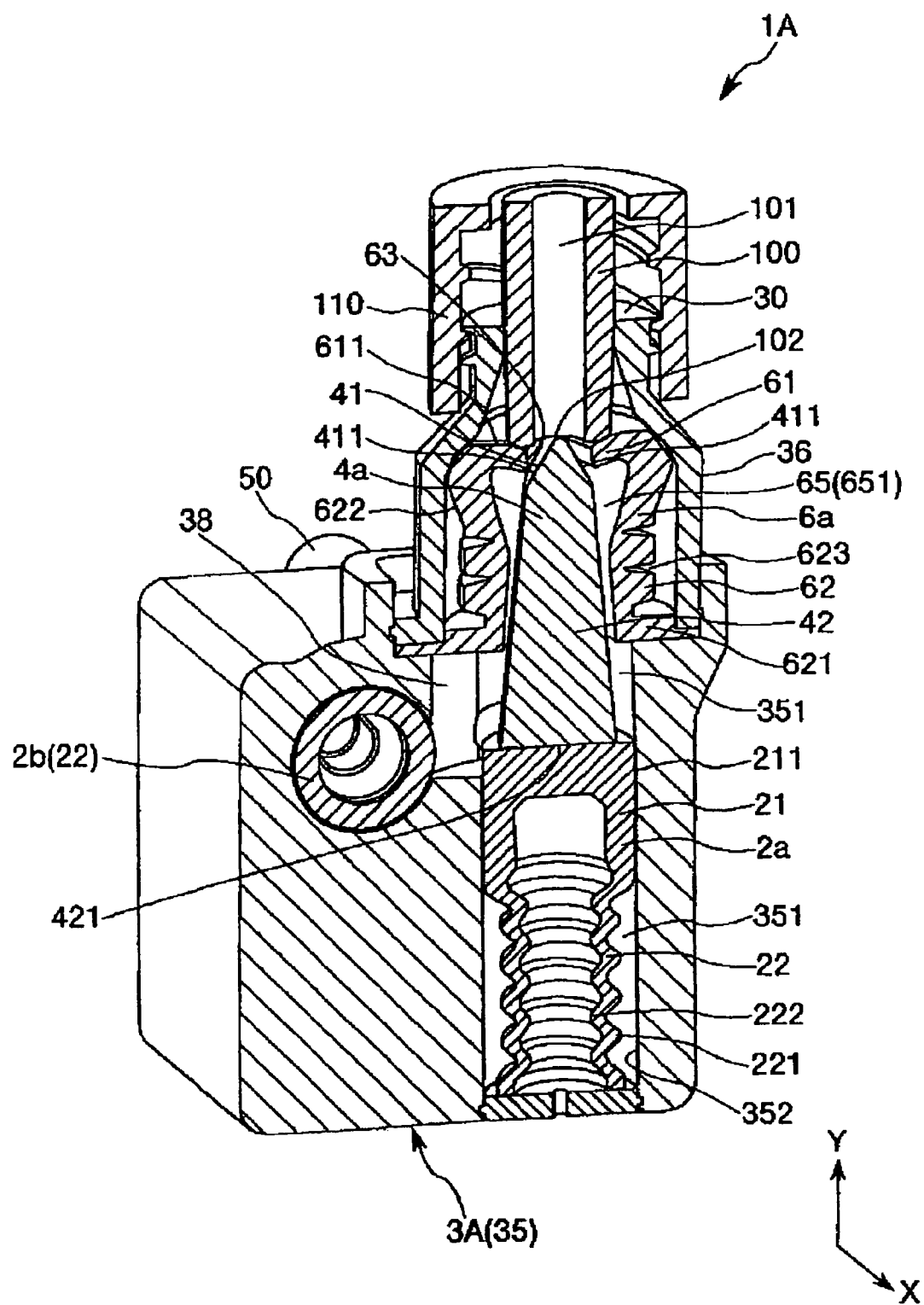
FIG. 5 is a sectional view taken along line B-B of FIG. 1 in the condition where a tube is connected to the connector.
Figure 6:
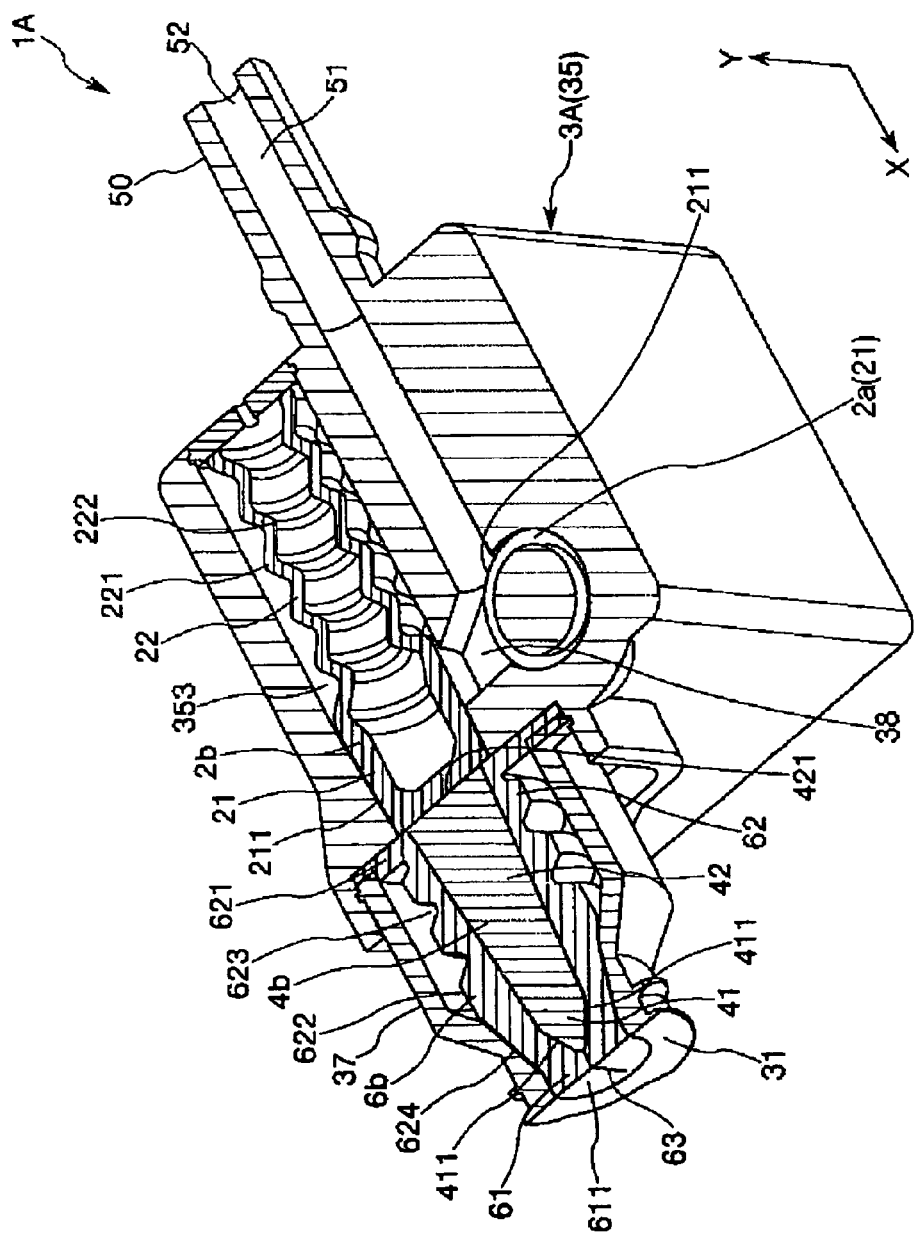
FIG. 6 is a sectional view taken along line A-A of FIG. 1 in the condition where the tube is connected to the connector.
Figure 7:
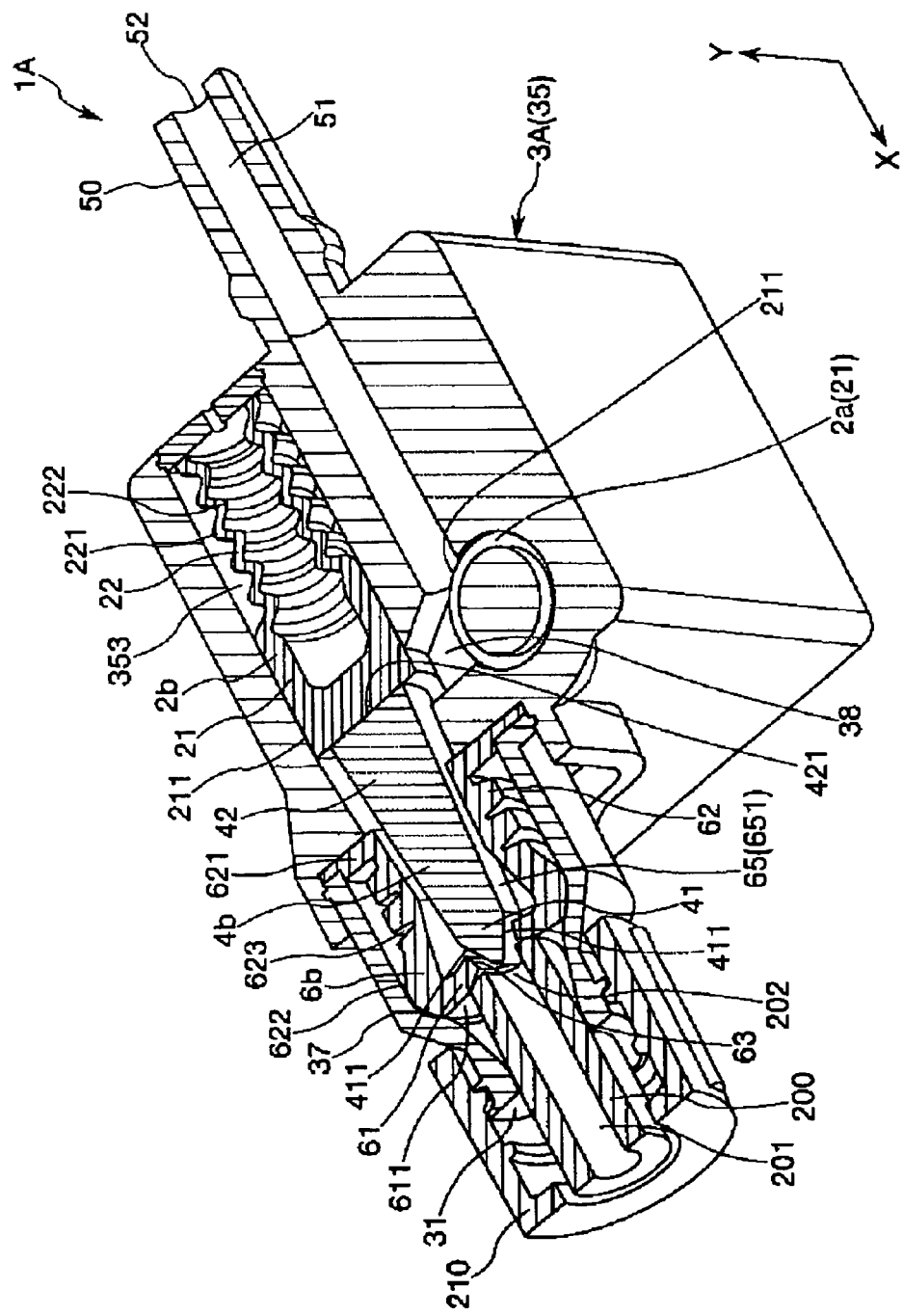
FIG. 7 is a sectional view taken along line A-A of FIG. 1 in the condition where the tube is connected to the connector.
Figure 8:
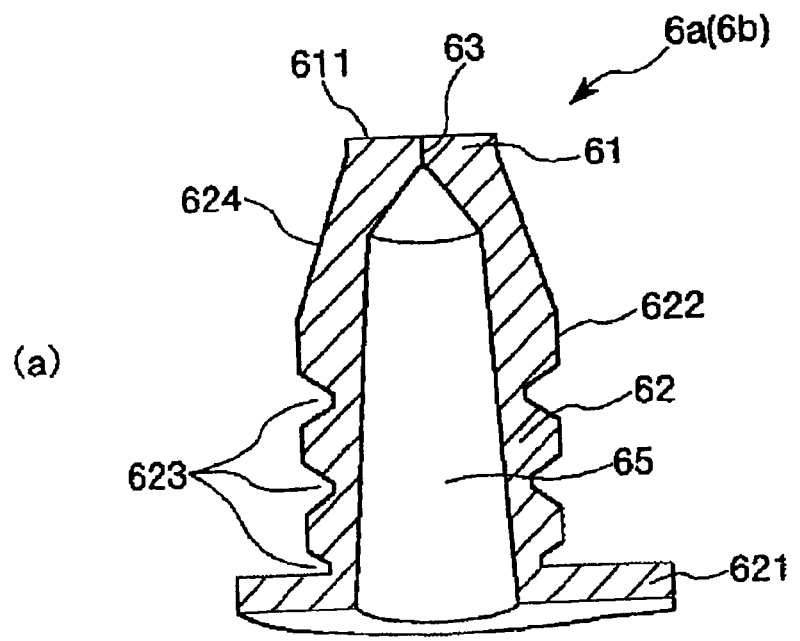
FIG. 8 shows a longitudinal sectional view (a) of a valve disk, and a perspective view (b) of a pin, the valve disk and the pin being possessed by a connecting section shown in FIG. 1.
Figure 8:
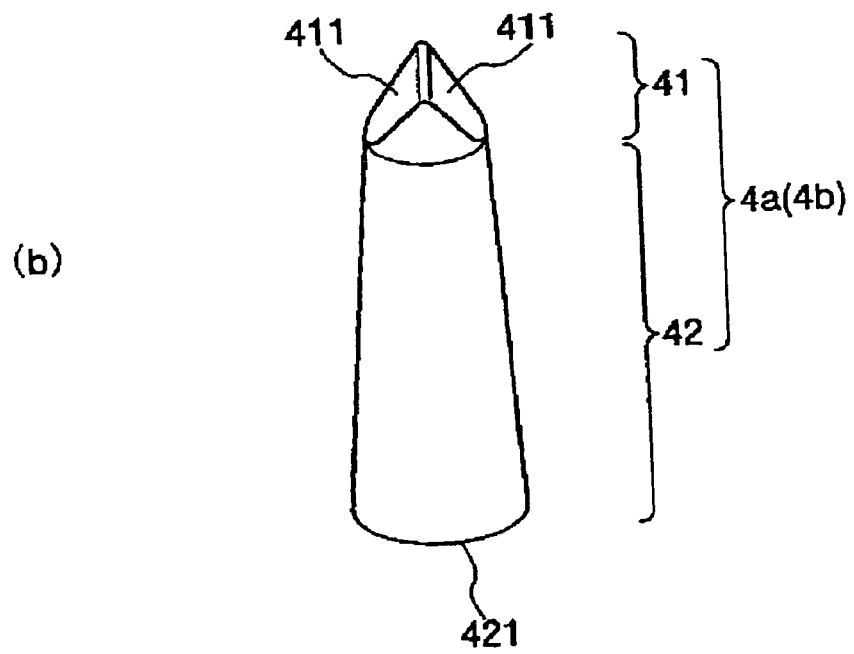

FIG. 1 is a perspective view showing a first embodiment of the connector according to the present invention; FIG. 2 is a sectional view taken along line A-A of FIG. 1; FIG. 3 is a sectional view taken along line B-B of FIG. 1; FIG. 4 is a sectional view taken along line A-A of FIG. 1 in the condition where a tube is connected to the connector; FIG. 5 is a sectional view taken along line B-B of FIG. 1 in the condition where a tube is connected to the connector; FIGS. 6 and 7 are each a sectional view taken along line A-A of FIG. 1 in the condition where a tube is connected to the connector; and FIG. 8 shows a longitudinal sectional view (a) of a valve disk, and a perspective view (b) of a pin, the valve disk and the pin being possessed by the connecting section shown in FIG. 1.

The connector 1A shown in these figures is for use in the state of being mounted in a medical appliance needing connection of liquid passages such as, for example, an infusion set (transfusion set), a nutiritive set, a pressure monitoring line, an artificial lung circuit, an artificial dialysis circuit, etc.

As shown in FIG. 1, the connector 1A includes a housing 3A, and a first valve disk 6a and a second valve disk 6b which are contained in the housing 3A.

The housing 3A has a main body 35 substantially cubic in shape, a first cap 36, a second cap 37, and a male-side connecting section 50.

The first cap 36 is substantially tubular in shape, and is provided on its one end side with a first female-side connecting port 30 capable of receiving a tube.

The second cap 37 is substantially tubular in shape, and is provided on its one end side with a second female-side connecting port 31 capable of receiving a tube.

As shown in FIGS. 2 and 3, the first female-side connecting port 30 (the first cap 36) and the second female-side connecting port 31 (the second cap 37) are provided with the first valve disk 6a and the second valve disk 6b, respectively. In addition, the first female-side connecting port 30 and the second female-side connecting port 31 are each so configured that a tube constituting a passage (for example, a tip projecting portion of a syringe, or a hub or sheath which itself is independent) can be connected thereto by insertion.

The center line of the first female-side connecting port 30 and the center line of the second female-side connecting port 31 are located in correlation of skew lines, and form an angle of about 90°. In the following description, the direction parallel to the center line of the first female-side connecting port 30 will be referred to as "the Y-axis direction", and the direction parallel to the center line of the second female-side connecting port 31, i.e., the direction perpendicular to the Y-axis direction will be referred to as "the X-axis direction".

The male-side connecting section 50 is a tubular member provided therein with a passage 51, and is so disposed that its center line is in the X-axis direction. The male-side connecting section 50 forms a lure taper gradually decreasing in outside diameter toward the tip thereof. The male-side connecting section 50 can be inserted into and connected to female-side connecting ports of other appliances (for example, a proximal end mouth of a catheter hub). In addition, the interior of the male-side connecting section 50 communicates with a liquid circulation space 38 which will be described later (see FIG. 2).

The connector 1A as above-described may be used in the condition where a plurality of the connectors 1A are collected and linked by inserting and connecting the male-side connecting section 50 of each connector 1A to the second female-side connecting port 31 of another connector 1A. In this case, since the second female-side connecting port 31 and the male-side connecting section 50 are provided in parallel and in the opposite directions, the plurality of the connectors 1A can be linked rectilinearly, and can be linked in such a shape as to promise easy use thereof.

The first valve disk 6a and the second valve disk 6b are each formed of elastic material. The elastic material is not particularly limited. Examples of the elastic material include various rubber materials such as silicone rubber, etc. and various thermoplastic resins such as polybutadiene, EVA, styrene-based elastomer, etc. Incidentally, the first valve disk 6a and the second valve disk 6b are substantially the same in shape and operation, and, therefore, the first valve disk 6a will be representatively described below.

As shown in FIGS. 3 and 8(*a*), the first valve disk 6a is composed of a substantially cylindrical barrel 62 of which the center line is directed in parallel to the Y-axis direction, and a top (head) 61 formed on one end side of the barrel 62.

The barrel 62 is provided therein with a pin insertion space (hollow section) 65 having a shape corresponding to the shape of a pin 4a which will be described later.

In addition, a flange 621 enlarged in outside diameter as compared with the barrel 62 is formed on the other end side of the barrel 62. When the first valve disk 6a is installed (contained) in the housing 3A, the flange 621 is clamped between the first cap 36 and the main body 35. This ensures that the first valve disk 6a is assuredly fixed (in a liquid-tight condition) in the housing 3A (see FIG. 3).

Besides, the outer peripheral surface 622 of the barrel 62 is provided with a plurality (three, in this embodiment) of grooves 623 along the whole circumference on the side of the flange 621. This ensures that when the first valve disk 6a is compressed in the axial direction (the Y-axis direction), the barrel 62 can easily be elastically deformed in the Y-axis direction (see FIG. 5).

In addition, the first valve disk 6a (the barrel 62) is provided on the top 61 side thereof with a taper 624 gradually decreasing in outside diameter toward the top 61. This ensures that when no tube is connected to the first female-side connecting port 30, the taper 624 abuts on the inside surface of the first cap 36, whereby the top 61 (the top face 611) can be prevented from protruding from the first female-side connecting port 30, i.e., the height of the top face 611 in the Y-axis direction can be restricted (see FIG. 3).

The top 61 is provided with a top slit 63 extending (penetrating) from the top face 611 to the pin insertion space 65. Incidentally, the top slit 63 may be formed so as to be closed, or so as to be opened, in the natural state of the first valve disk 6a (the top 61).

As shown in FIGS. 2 and 3, the connector 1A is provided further with solid pins 4a and 4b which are located (inserted) in the pin insertion space 65 of the first valve disk 6a and in the pin insertion space 65 of the second valve disk 6b, respectively. In addition, the pins 4a and 4b are each installed movably in the housing 3A.

As shown in FIG. 3, in the condition where a male lure (tube) 100 is not connected to the first female-side connecting port 30 (hereinafter referred to as "the non-connected condition"), the pin insertion space 65 in the first valve disk 6a is substantially wholly filled up with the pin 4a. This prevents a liquid from stagnating in the pin insertion space 65. In addition, since the pin 4a is a solid member not having any hollow section, stagnation of a liquid in the pin 4a is also prevented.

Besides, as shown in FIG. 2, also in the condition where a male lure (tube) 200 is not connected to the second female-side connecting port 31 (hereinafter referred to as "the non-connected condition"), similarly, the pin insertion space 65 in the second valve disk 6b is substantially entirely filled up with the pin 4b. This prevents a liquid from stagnating in the pin insertion space 65. In addition, since the pin 4b is a solid member not having any hollow section, stagnation of a liquid in the pin 4b is also prevented.

Incidentally, since the pins 4a and 4b are substantially the same in shape and operation, the pin 4a will be representatively described below.

As shown in FIGS. 3 and 8(*b*), the pin 4a has a top 41 and a tapered part (trunk) 42.

The tapered part 42 is a part, gradually decreasing in outside diameter toward the top 41, of the pin 4a. As shown in FIG. 5, when the male lure 100 is connected to the first female-side connecting port 30 (this condition will hereinafter be referred to as "the connected condition") and the pin 4a is moved in the Y-axis direction, a clearance 651 is assuredly generated between the inside of the barrel 62 of the first valve disk 6a and the tapered part 42.

In addition, in the connected condition, the top 41 abuts on the mouth 102 of the tube 100, but the top 41 is so shaped as not to close the mouth 102 of the tube 100. Specifically, the top 41 is provided with two slant faces 411 inclined against the Y-axis direction (the axial direction). In addition, these two slant faces 411 are so provided that the top 41 is substantially triangular in longitudinal sectional shape (see, for example, FIG. 5).

With the top 41 formed in such a shape, in the connected condition, the top 41 (the pin 4a) can easily enter into the top slit 63 and, therefore, the top slit 63 can be opened more assuredly. Besides, in the connected condition, communication between a passage 101 in the male lure 100 and the clearance 651 (the pin insertion space 65) is established through the top slit 63 thus opened.

As shown in FIGS. 2 and 3, the connector 1A is provided further with urging sections 2a and 2b for urging the pins 4a and 4b in the Y-axis direction and the X-axis direction, respectively. Incidentally, since the urging sections 2a and 2b are substantially the same in shape and operation, the urging section 2a will be representatively described below.

As shown in FIG. 3, the urging section 2a has an abutting part (head) 21 which abuts on a bottom face 421 of the tapered part 42 of the pin 4a, and a barrel 22 formed on one end side of the abutting part 21. The urging section 2a is contained in a cylindrical space 351 formed inside the main body 35 of the housing 3A.

The abutting part 21 is cylindrical in outside shape. In addition, the abutting part 21 is formed to have an outside diameter approximately equal to the inside diameter of the space 351. This ensures that close contact is established between an outer peripheral surface 211 of the abutting part 21 and an inner peripheral surface 352 surrounding the space 351; therefore, in the connected condition, a liquid having flowed into the space 351 through the clearance 651 can be prevented from flowing further to the depth side (the barrel 22 side) of the space 351 (see FIG. 5). Accordingly, during when a liquid flows, the liquid can be prevented from stagnating.

The barrel 22 is composed of a bellows-like tubular body. Specifically, the barrel 22 assumes a bellows-like form in which large-diameter ring parts 221 and small-diameter ring parts 222 are alternately arranged along the Y-axis direction. Such a barrel 22 functions as an urging means for urging the pin 4a in the Y-axis direction (the direction in which the pin 4a is inserted into the pin insertion space 65).

In addition, while the barrel 22 is in charge of most of the urging force for urging the pin 4a to move toward the pin insertion space 65, the abutting part 21 may in charge of part of the urging force.

Besides, the material constituting the urging parts 2a and 2b is not particularly limited; for example, the materials mentioned above in relation to the first valve disk 6a and the second valve disk 6b can be used.

As shown in FIGS. 2 and 3, the liquid circulation space (inner cavity) 38 through which a liquid passes is formed in the inside of the housing 3A. The liquid circulation space 38 is so shaped that during when a liquid flows therethrough, stagnation of the liquid there is restrained as assuredly as possible. In other words, the liquid circulation space 38 is so shaped as not to have any cove-like portion where a liquid might stagnate.

The set of the first valve disk 6a, the pin 4a and the urging section 2a and the set of the second valve disk 6b, the pin 4b and the urging section 2b are so arranged that the center axes of the two sets are located in correlation of skew lines. This configuration has the merit that the volume of the liquid circulation space 38 can be made extremely small, as compared with the case where the center axes of the two sets intersect each other on a plane.

In addition, the set of the first valve disk 6a, the pin 4a and the urging section 2a and the set of the second valve disk 6b, the pin 4b and the urging section 2b share the liquid circulation space 38. Namely, side parts of the two sets are connected to each other through the liquid circulation space 38. This ensures that even when a liquid flows from the side of the first valve disk 6a into the liquid circulation space 38 or flows from the side of the second valve disk 6b into the liquid circulation space 38, the liquid will pass through the liquid circulation space 38, so that stagnation of the liquid can be prevented from occurring.

In the non-connected condition, the top 61 of the first valve disk 6a is inserted in the first female-side connecting port 30 (see FIG. 3). The inside diameter of the first female-side connecting port 30 is slightly smaller than the outside diameter of the top 61 in its natural state. This ensures that in the non-connected condition, the top 61 is fastened in the radial directions, whereby the top slit 63 is closed more securely.

Besides, in the non-connected condition, the top 61 of the second valve disk 6b is inserted in the second female-side connecting port 31 (see FIG. 2). The inside diameter of the second female-side connecting port 31 is slightly smaller than the outside diameter of the top 61 in its natural state. This ensures that in the non-connected condition, the top 61 is fastened in the radial directions, whereby the top slit 63 is closed more securely.

Now, the condition where a male lure 100 of, for example, an infusion set or the like is connected to the first female-side connecting port 30 will be described below, based on FIGS. 5, 6 and 7.

As shown in FIG. 5, at the time of connecting the male lure 100 to the first female-side connecting port 30, the housing 3A is gripped and a tip portion of the male lure 100 is inserted progressively into the first female-side connecting port 30. During this operation, the tip face of the male lure 100 presses the top face 611 (the top 61) of the first valve disk 6a, causing the barrel 62 of the first valve disk 6a to contract accordingly. Simultaneously, the top 41 of the pin 4a is pressed, causing the pin 4a to move in the Y-axis direction. This movement generates a clearance 651 in the first valve disk 6a, resulting in that communication between the clearance 651 and the liquid circulation space 38 is established through the space 351 in the housing 3A.

Besides, in this instance, the urging section 2a (the barrel 22) is compressed, so that by the urging force of the urging section 2a thus compressed, the top 41 of the pin 4a is inserted into the top slit 63, enlarging the top slit 63 pushingly. Then, the top 41 of the pin 4a abuts on the mouth 102 of the male lure 100, to enlarge the top slit 63 more assuredly, establishing communication between the top slit 63 and the passage 101 in the male lure 100.

Upon the connection as just-mentioned, as shown in FIG. 5 and FIG. 6 (FIG. 7), the passage 101 in the male lure 100 communicates with the passage 51 in the male-side connecting section 50 through the top slit 63, the pin insertion space 65 (the clearance 651) in the first valve disk 6a, the space 351 in the housing 3A, and the liquid circulation space 38.

As mentioned above, since the pin 4a is movable in the housing 3A, the length of insertion of the pin 4a into the top slit 63 is constant. This ensures that the top slit 63 of the first valve disk 6a is prevented from being broken, and the liquid-tightness at the top slit 63 is obtained sustainedly.

Incidentally, the male lure 100 is fixed by being fitted in the inner periphery of the first female-side connecting port 30. In addition, the first female-side connecting port 30 is provided with a male screw at its outer periphery, so that the male lure 100 can be fixed thereto more securely by a screw-type lock 110.

In the connected condition shown in FIGS. 5 to 7, when a liquid such as a liquid medicine is let flow from the passage 101 of the male lure 100, the liquid passes successively through the top slit 63, the pin insertion space 65 in the first valve disk 6a, the space 351 in the housing 3A, the liquid circulation space 38, and the passage 51 in the male-side connecting section 50, to flow out through the mouth 52 of the male-side connecting section 50. In this instance, as best seen from FIG. 6, the space 353 capable of communicating with the liquid circulation space 38 is closed, so that the liquid is prevented from flowing to the side of the second valve disk 6b. In addition, since the liquid circulation space 38 is so shaped as to prohibit stagnation (so shaped as not to have a cove-like part), substantially the whole amount of the liquid flowing in through the passage 101 in the male lure 100 will flow into the male-side connecting section 50, without stagnating. A tube (not shown) is preliminarily connected to the male-side connecting section 50, and the liquid can be let flow through the tube to the patient side.

Besides, in the case of replacing air in the liquid circulation space 38 by a liquid such as a liquid medicine, air is not liable to remain in the liquid circulation space 38, so that the replacement of air by the liquid, i.e., priming, can be performed more assuredly.

When the male lure 100 in the connected condition shown in FIGS. 6 to 8 is detached, the first valve disk 6a is restored, by the restoring force (the urging force) of the barrel 62, to a position where the top 61 of the first valve disk 6a is fastened by the inner periphery of the first female-side connecting port 30. As a result, the top slit 63 is closed. Besides, under the restoring force (the urging force) of the urging section 2a, the pin 4a is returned to a position such as to substantially entirely fill up the pin insertion space 65 in the first valve disk 6a. In this manner, the connector 1A is returned into the non-connected condition shown in FIG. 3.

In the next place, the condition where a male lure 200 of, for example, an infusion set or the like is connected to the second female-side connecting port 31 will be described below, based on FIG. 4.

As shown in FIG. 4, at the time of connecting the male lure 200 to the second female-side connecting port 31, the housing 3A is gripped, and a tip part of the male lure 200 is inserted progressively into the second female-side connecting port 31. During this operation, the tip face of the male lure 200 presses the top face 611 (the top 61) of the second valve disk 6b, causing the barrel 62 of the second valve disk 6b to contract accordingly. Simultaneously, the top 41 of the pin 4b is pressed, causing the pin 4b to move in the X-axis direction. This movement generates a clearance 651 in the second valve disk 6b, resulting in that communication between the clearance 651 and the liquid circulation space 38 is established through the space 353 in the housing 3A.

Besides, in this instance, the urging section 2b (the barrel 22) is compressed, so that by the urging force of the urging section 2b thus compressed, the top 41 of the pin 4b is inserted into the top slit 63, enlarging the top slit 63 pushingly. Then, the top 41 of the pin 4b abuts on the mouth 202 of the male lure 200, to enlarge the top slit 63 more assuredly, establishing communication between the top slit 63 and the passage 201 in the male lure 200.

Upon the connection as just-mentioned, as shown in FIG. 4, the passage 201 in the male lure 200 communicates with the passage 51 in the male-side connecting section 50 through the top slit 63, the pin insertion space 65 (the clearance 651) in the second valve disk 6b, the space 353 in the housing 3A, and the liquid circulation space 38.

As mentioned above, since the pin 4b is movable in the housing 3A, the length of insertion of the pin 4b into the top slit 63 is constant. This ensures that the top slit 63 of the first valve disk 6b is prevented from being broken, and the liquid-tightness at the top slit 63 is obtained sustainedly.

Incidentally, the male lure 200 is fixed by being fitted in the inner periphery of the second female-side connecting port 31. In addition, the second female-side connecting port 31 is provided with a male screw at its outer periphery, so that the male lure 200 can be fixed thereto more securely by a screw-type lock 210.

In the connected condition shown as just-mentioned, when a liquid such as a liquid medicine is let flow from the passage 201 of the male lure 200, the liquid passes successively through the top slit 63, the pin insertion space 65 in the second valve disk 6b, the space 353 in the housing 3A, the liquid circulation space 38, and the passage 51 in the male-side connecting section 50, to flow out through the mouth 52 of the male-side connecting section 50. In this instance, the space 351 capable of communicating with the liquid circulation space 38 is closed, so that the liquid is prevented from flowing to the side of the first valve disk 6a. In addition, since the liquid circulation space 38 is so shaped as to prohibit stagnation (so shaped as not to have a cove-like part), substantially the whole amount of the liquid flowing in through the passage 201 in the male lure 200 will flow into the male-side connecting section 50, without stagnating.

When the male lure 200 in the connected condition just-mentioned is detached, the second valve disk 6b is restored, by the restoring force (the urging force) of the barrel 62, to a position where the top 61 of the second valve disk 6b is fastened by the inner periphery of the second female-side connecting port 31. As a result, the top slit 63 is closed. Besides, under the restoring force (the urging force) of the urging section 2b, the pin 4b is returned to a position such as to substantially entirely fill up the pin insertion space 65 in the second valve disk 6b. In this manner, the connector 1A is returned into the non-connected condition shown in FIG. 2.

While the case where the male lure 100 or 200 is connected to one of the first female-side connecting port 30 and the second female-side connecting port 31 has been described above, the connector 1A can naturally be used in the condition where both the male lures 100 and 200 are simultaneously connected to the first female-side connecting port 30 and the second female-side connecting port 31, respectively (see FIG. 7).

In the case where the male lures 100 and 200 are connected respectively to both the first female-side connecting port 30 and the second female-side connecting port 31, it is possible, for example, to let different liquids to flow into the connector 1A respectively through the passage 101 in the male lure 100 and the passage 201 in the male lure 200. The liquids flowing in respectively through the passages 101 and 201 mix with each other in the liquid circulation passage 38, and the liquid mixture flows out through the mouth 52 of the male-side connecting section 50. In the case where, for example, the male lure 100 is detached from the connector 1A (the first female-side connecting port 30) after the flow-in of the liquid from the male lure 100 into the connector 1A is finished, the liquid in the pin insertion space 65 of the first valve disk 6a and the space 351 of the housing 3A is pushed out to the side of the male-side connecting section 50, due to the restoration of these component parts. This prevents the liquid in the male lure 100 from stagnating. In the case where, for example, the male lure 200 is detached from the connector 1A (the second female-side connecting port 31) after the flow-in of the liquid from the male lure 200 into the connector 1A is finished, similarly, the liquid in the pin insertion space 65 of the second valve disk 6b and the space 353 of the housing 3A is pushed out to the male-side connecting section 50, due to the restoration of these component parts. This prevents the liquid in the male lure 200 from stagnating.

In the connector 1A as above-described, the phenomenon in which the liquid in the passage 51 is pushed out through the mouth 52 (positive flow) when the male lure 100 and/or the male lure 200 is connected and the phenomenon in which the liquid is sucked through the mouth 52 into the passage 51 (backflow) when the male lure 100 and/or the male lure 200 is evulsed can be prevented from occurring, and troubles due to such phenomena can be prevented from occurring.

In addition, the materials of the housing 3A and the pins 4a and 4b are not particularly limited, but materials having appropriate hardness are preferably used. Examples of the usable material include polymeric materials such as polyethylene, polypropylene, and polycarbonate.

Besides, while the configuration having two female-side connecting ports has been described in this embodiment, the connector according to the present invention may have three or more female-side connecting ports.

Second Embodiment

Figure 11:
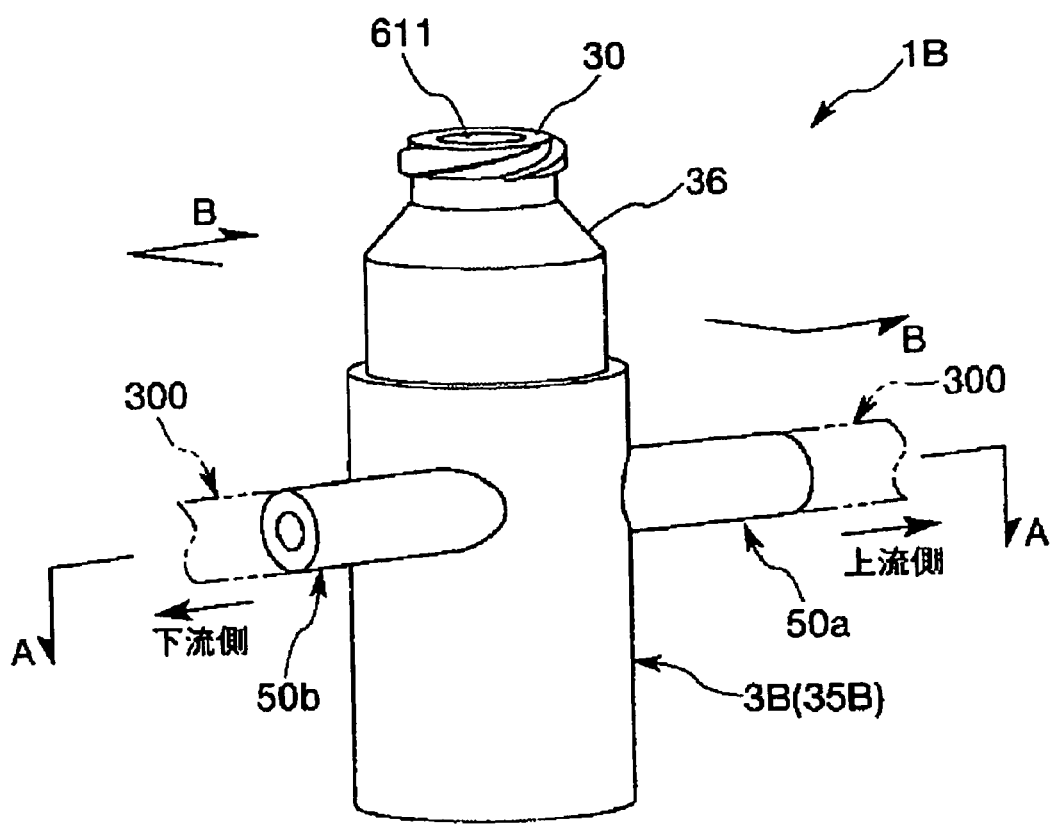
FIG. 11 is a perspective view showing a second embodiment of the connector according to the present invention.
Figure 12:
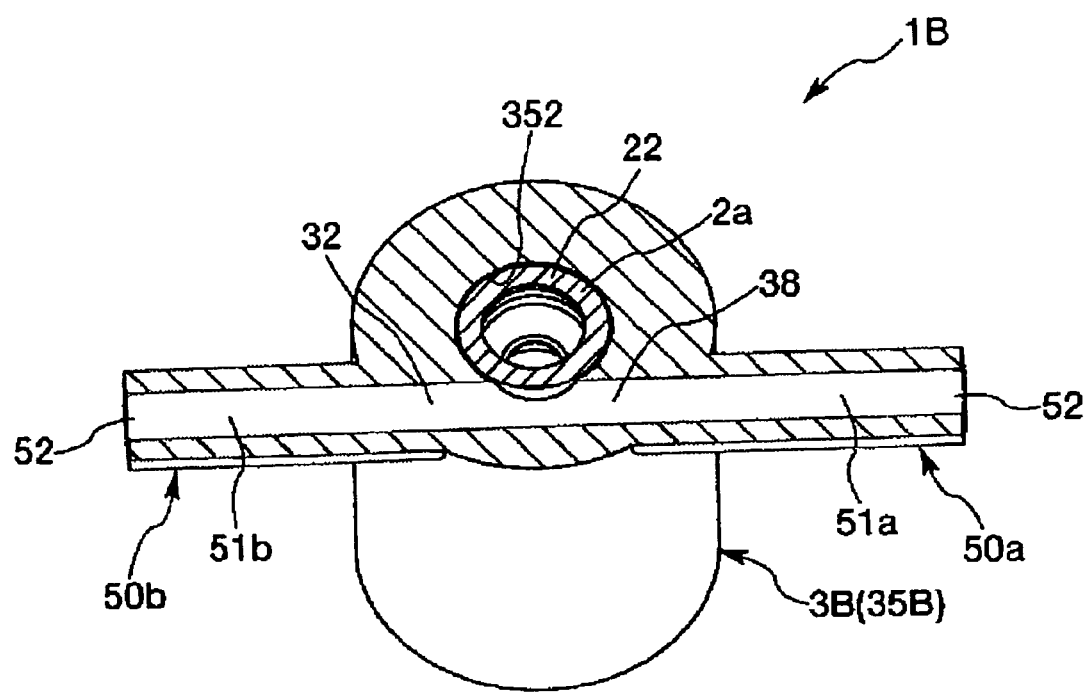
FIG. 12 is a sectional view taken along line A-A of FIG. 11.
Figure 13:
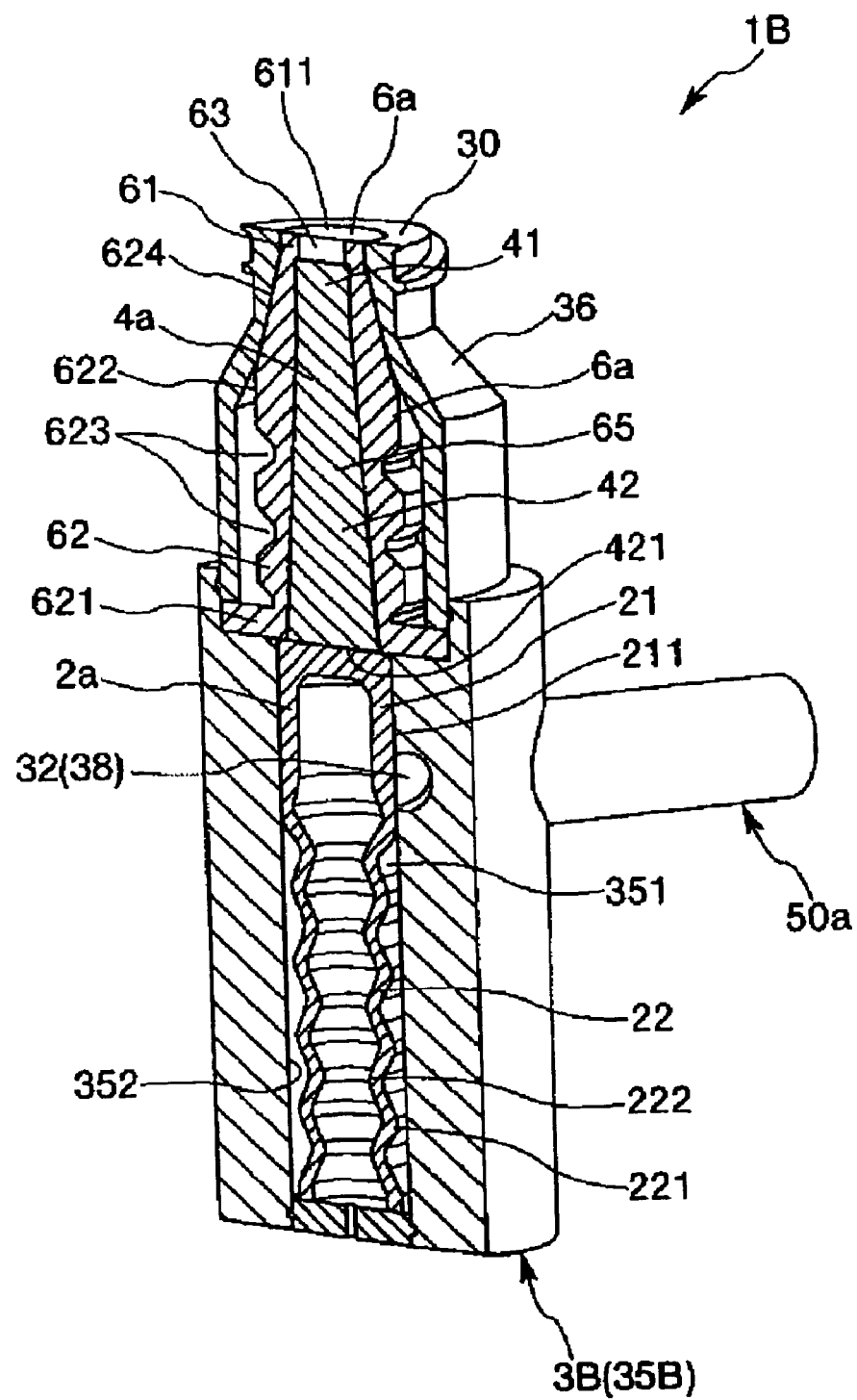
FIG. 13 is a sectional view taken along line B-B of FIG. 11.

FIG. 11 is a perspective view showing a second embodiment of the connector according to the present invention; FIG. 12 is a sectional view taken along line A-A of FIG. 11; and FIG. 13 is a sectional view taken along line B-B of FIG. 11.

Now, the second embodiment of the connector according to the present invention will be described below referring to these figures. The following description will be centered on the differences of this embodiment from the first embodiment described above, and description of the same items as above will be omitted.

This embodiment is the same as the first embodiment described above, except for the configuration of the housing.

As shown in FIG. 11, the connector 1B has a housing 3B, and a first valve disk 6a contained in the housing 3B.

The housing 3B has a main body 35B substantially cylindrical in shape, a first cap 36, a first male-side connecting section 50a, and a second male-side connecting section 50b.

As shown in FIG. 12, the first male-side connecting section 50a and the second male-side connecting section 50b communicate with each other through a liquid circulation space 38, and the male-side connecting sections are so formed that their center lines coincide with each other. Specifically, the first male-side connecting section 50a and the second male-side connecting section 50b are so formed that a space 32 composed of a passage 51a in the first male-side connecting section 50a, the liquid circulation space 38, and a passage 51b in the second male-side connecting section 50b is substantially cylindrical in shape. In addition, the center axis of the space 32 and the center axis of a space 351 in the housing 3B are in positional correlation of skew lines (see FIGS. 12 and 13).

The connector 1B configured in this manner can be used in the course of a passage (tube 300) through which a liquid flows (see FIG. 11). This permits the connector 1B to function as a mixing injection port installed in the course of the tube 300.

In this case, the first male-side connecting section 50a is located on the upstream side (the right side, in FIG. 11) of the tube 300 to which a roller klemme or a pin needle of an infusion set, for example, is connected, and the second male-side connecting section 50b is located on the downstream side (the left side, in FIG. 11) of the tube 300 to which a male lure, for example, is connected. Namely, the first male-side connecting section 50a is connected to the tube 300 on the upstream side, and the second male-side connecting section 50b is connected to the tube 300 on the downstream side.

With the connector 1B thus provided at an intermediate portion of the tube 300 and with the male lure 100 connected to the connector 1B, it is possible to inject a liquid into the tube 300, or drain a liquid from the tube 300, through the top slit 63, the pin insertion space 65 and the liquid circulation space 38 (see FIG. 13).

Incidentally, the first male-side connecting section 50a and the second male-side connecting section 50b are each not limited to one which constitutes a lure taper (male lure); for example, one of the male-side connecting sections may be provided with a mouth (female lure) like the first female-side connecting port 30 (the first cap 36).

In addition, while the configuration having one female-side connecting port and two male-side connecting sections has been described in this embodiment, the connector according to the present invention may have one female-side connecting port and one male-side connecting section.

Third Embodiment

Figure 14:
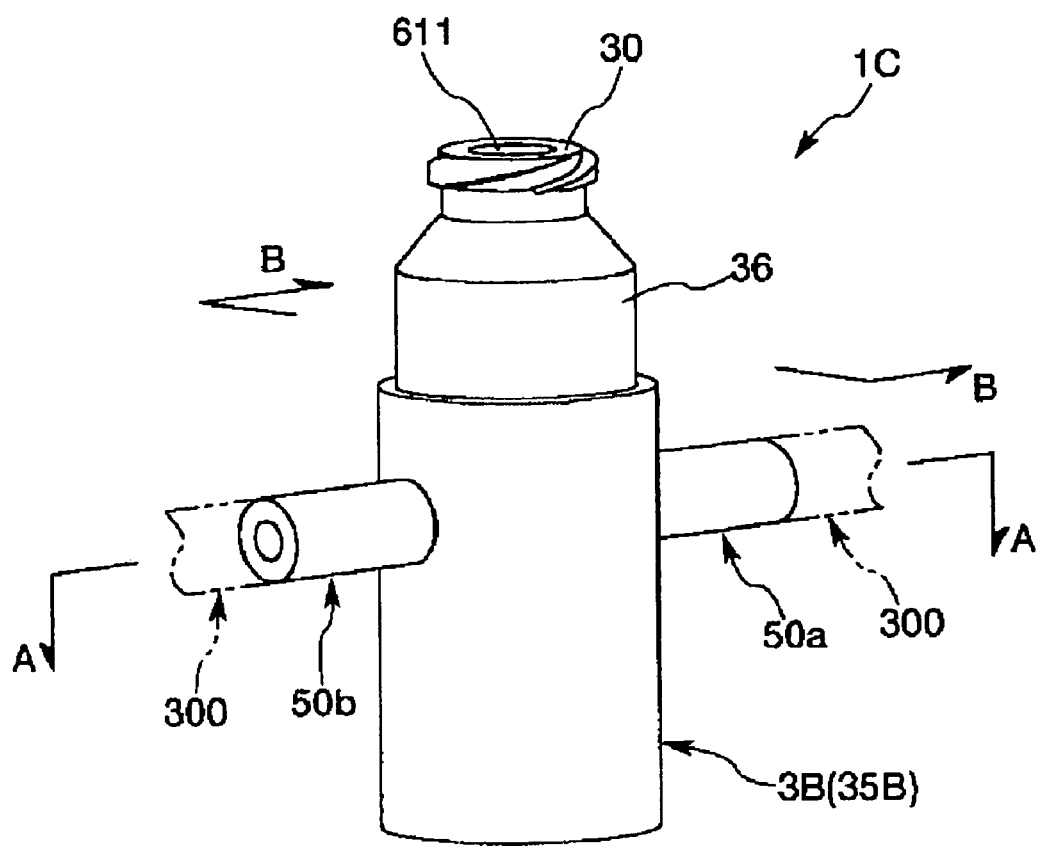
FIG. 14 is a perspective view showing a third embodiment of the connector according to the present invention.
Figure 15:
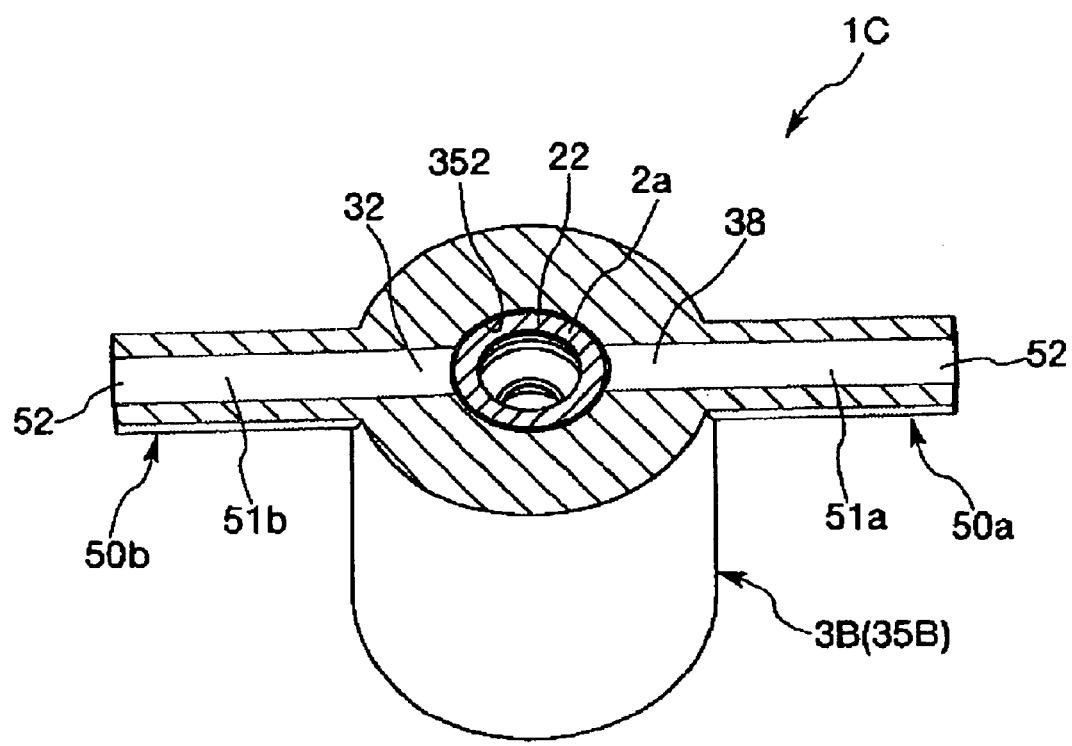
FIG. 15 is a sectional view taken along line A-A of FIG. 14.

FIG. 14 is a perspective view showing a third embodiment of the connector according to the present invention; FIG. 15 is a sectional view taken along line A-A of FIG. 14; and FIG. 16 is a sectional view taken alone ling B-B of FIG. 14.

Now, the third embodiment of the connector according to the present invention will be described below referring to these figures. The following description will be centered on the differences of this embodiment from the second embodiment described above, and description of the same items as above will be omitted.

This embodiment is the same as the second embodiment described above, except for the shape of the housing.

Figure 16:
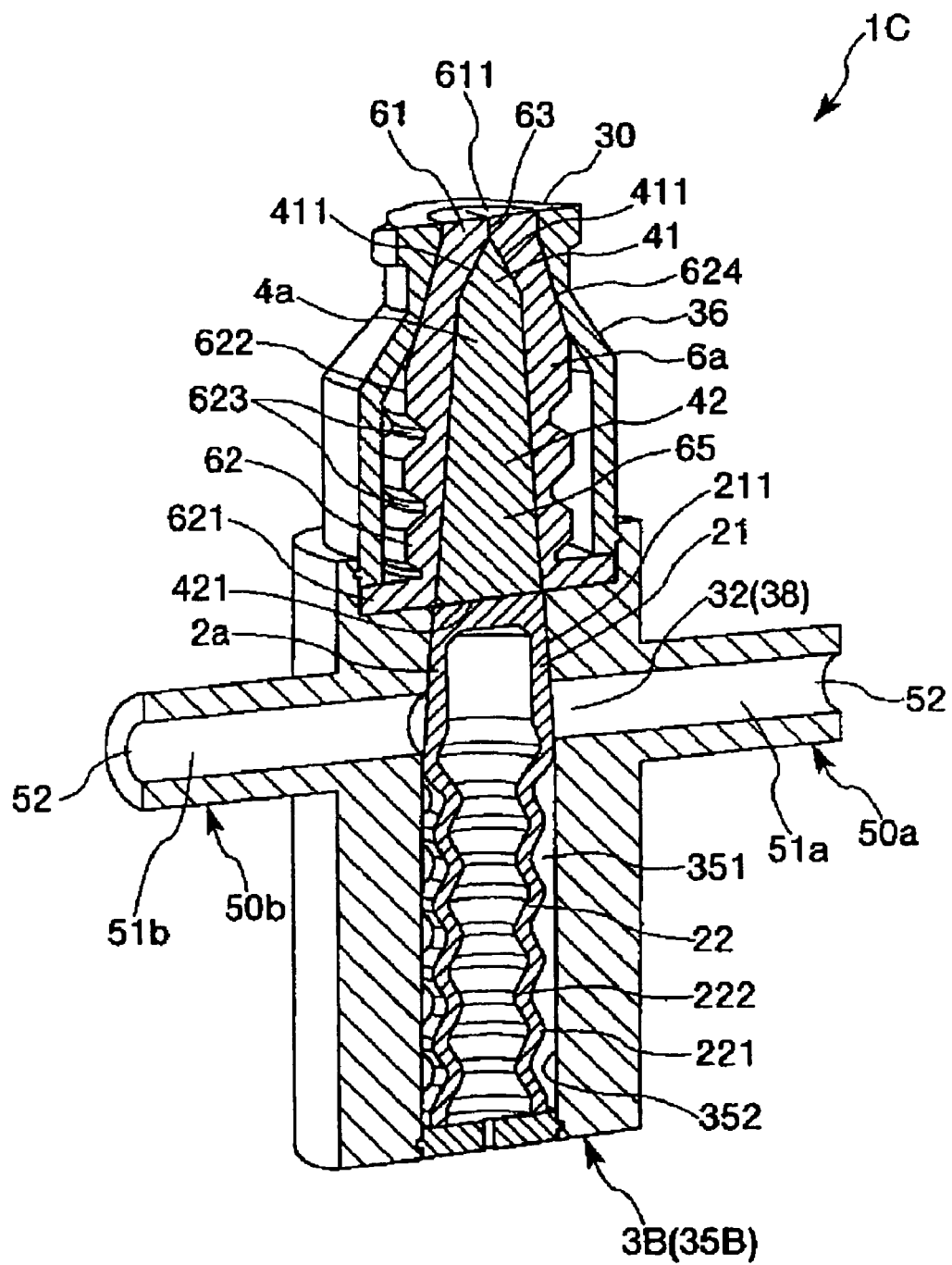
FIG. 16 is a sectional view taken along line B-B of FIG. 14.

As shown in FIGS. 15 and 16, in this connector 1C, the center axis of the space 32 and the center axis of the space 351 in the housing 3B are substantially orthogonal to each other.

In the non-connected condition, a liquid passing through the tube 300 can pass through the clearance (the space 351) between the inner peripheral surface 352 and the abutting part 21 (the barrel 22).

Besides, in the connected condition, a liquid from a tube 100 can be mixed into the liquid in the tube 300, through the connector 1C.

Fourth Embodiment

Figure 17:
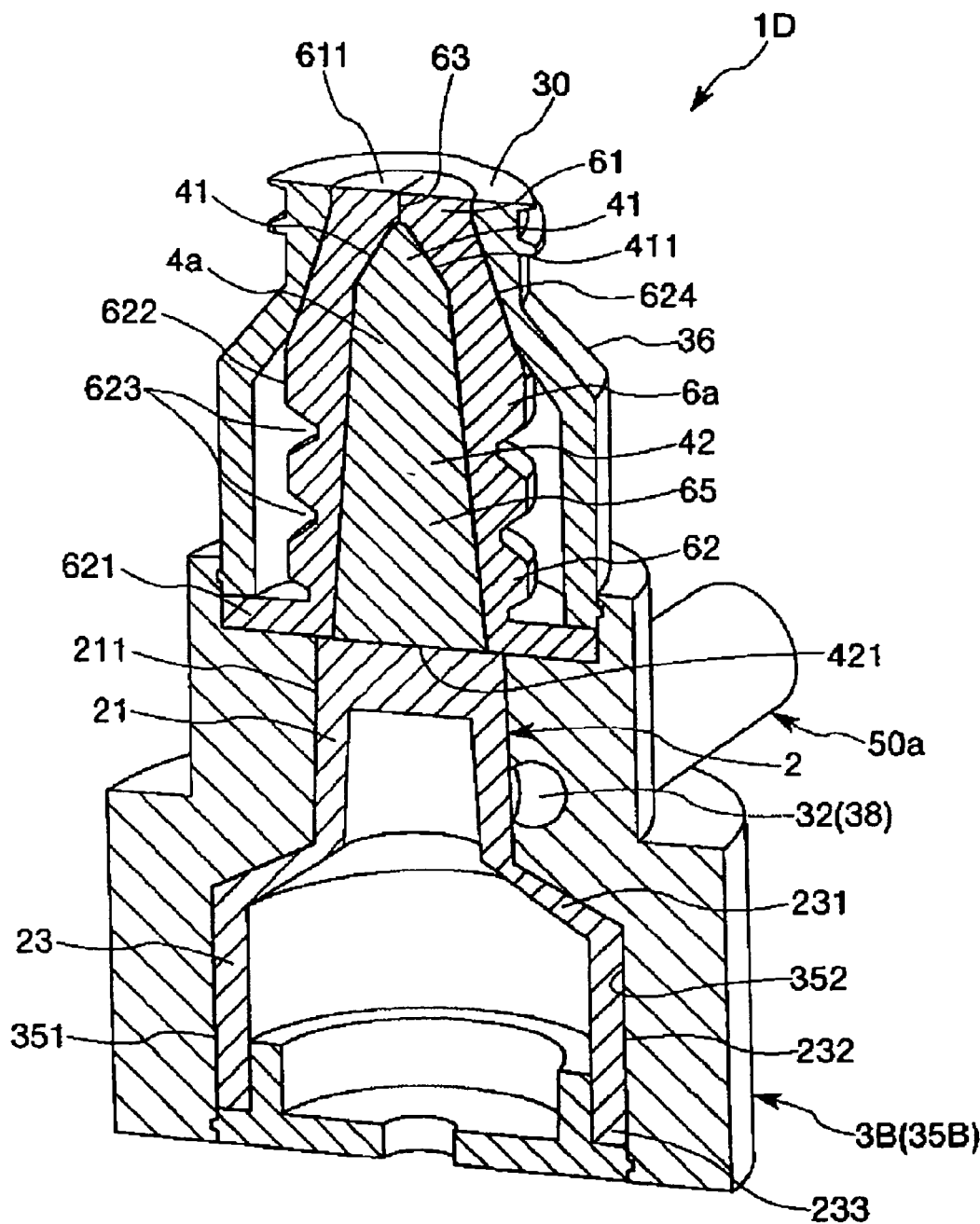
FIG. 17 is a longitudinal sectional view showing a fourth embodiment of the connector according to the present invention.

FIG. 17 is a longitudinal sectional view showing a fourth embodiment of the connector according to the present invention.

Now, the fourth embodiment of the connector according to the present invention will be described below referring to this figure. The following description will be centered on the differences of this embodiment from the second embodiment described above, and description of the same items as above will be omitted.

This embodiment is the same as the second embodiment described above, except for the shape of the urging section.

The urging section 2 of this connector 1D has an abutting part (head) 21, and a barrel 23 larger than the abutting part 21 in outside diameter.

The inside of the urging section 2 is hollow, and a shoulder part 231 of the barrel 23 is smaller in material thickness than the other parts of the barrel 23. This permits the shoulder part 231 to be deformed easily; therefore, in the connected condition, the shoulder part 231 is deformed to permit the abutting part 21 to easily move to the barrel 23 side, so that a liquid can pass through the interior of the connector 1D.

In addition, the urging section 2 is fixed to the housing 3B in a liquid-tight manner, at the lower end 233 of the barrel 23.

Besides, the outer peripheral surface 232 of the barrel 23 is in abutment on (close contact with) the inner peripheral surface 352 of the housing 3B. This abutting condition is maintained also in the connected condition, thereby preventing the liquid from flowing into the barrel 23 side of the space 351.

Fifth Embodiment

Figure 18:
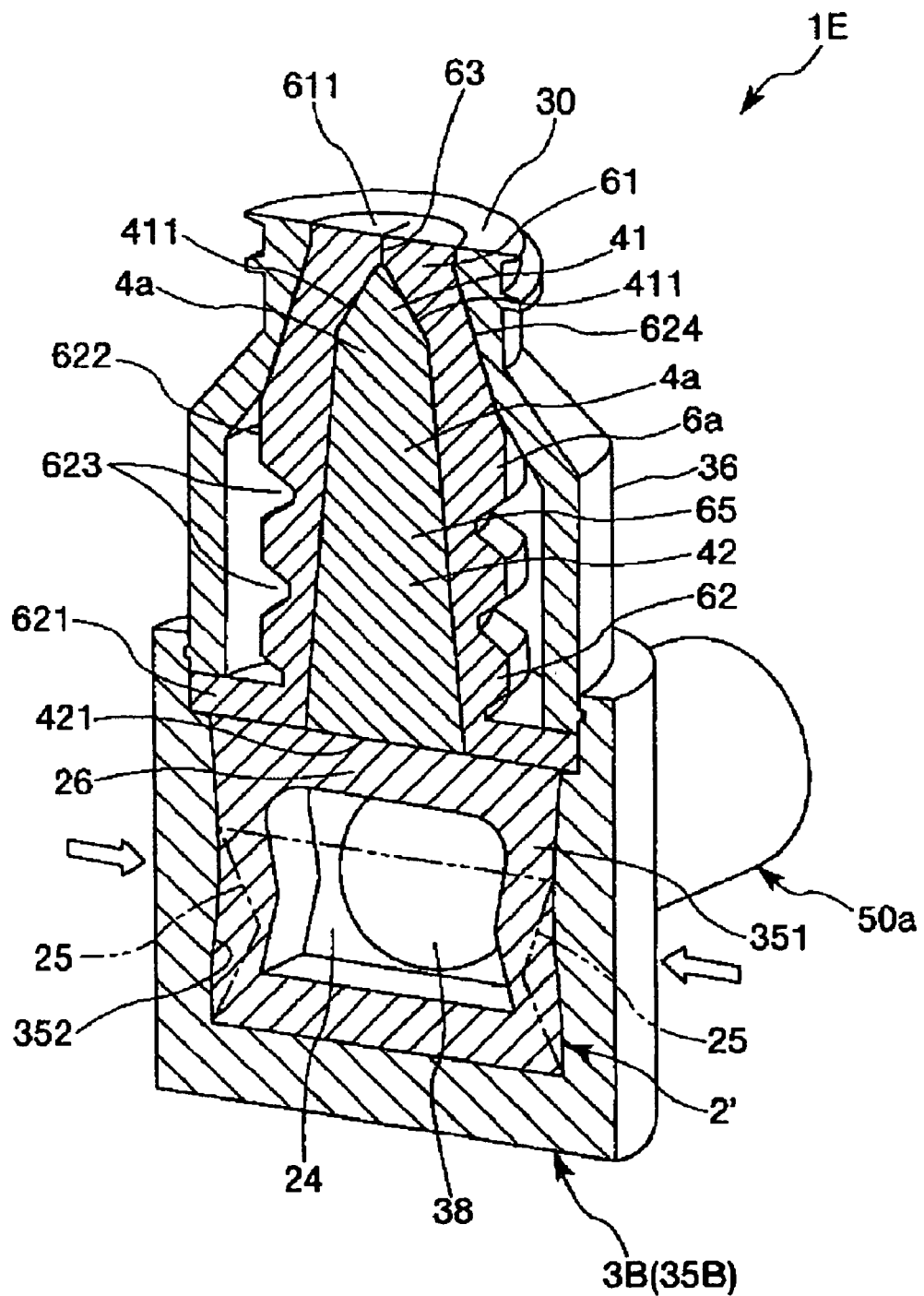
FIG. 18 is a longitudinal sectional view showing a fifth embodiment of the connector according to the present invention.
Figure 19:
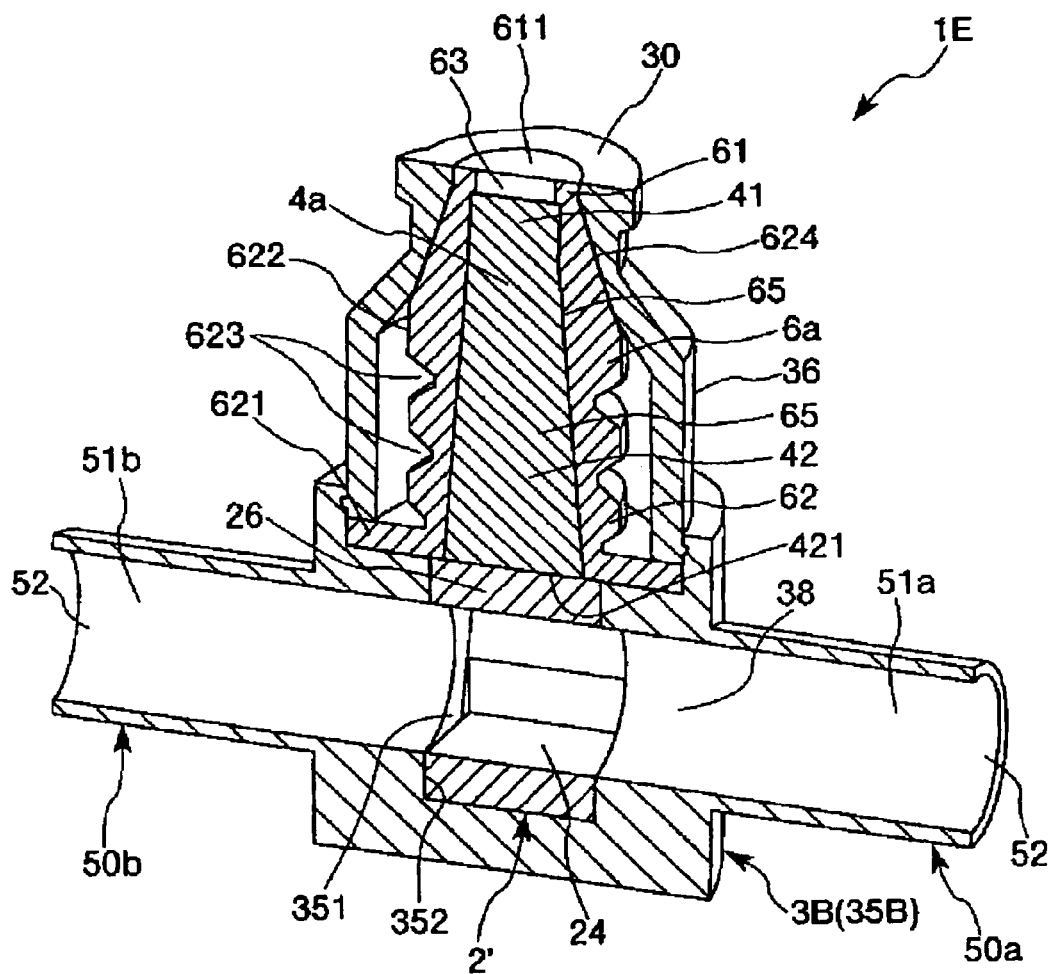
FIG. 19 is a longitudinal sectional view showing the fifth embodiment of the connector according to the present invention.

FIGS. 18 and 19 are longitudinal sectional views showing a fifth embodiment of the connector according to the present invention.

The following description will be centered on the differences of this embodiment from the second embodiment described above, and description of the same items as above will be omitted.

This embodiment is the same as the second embodiment described above, except for the shape of the urging section.

The urging section 2' of this connector 1E is block-like in shape. The urging section 2' is provided with a hollow section 24 penetrating it (see FIG. 18). The urging section 2' thus shaped is installed in a housing 3B so that the hollow section 24 communicates with the space 32 (the liquid circulation space 38) (see FIG. 19).

In the connected condition, the top 26 of the urging section 2' is pressed by the pin 4a, deforming a side part 25 of the urging section 2' so as to bend to the hollow section 24 side (in the directions of arrows in FIG. 19) (as indicated by two-dotted chain lines in FIG. 18). This establishes communication between the pin insertion space 65 in the first valve disk 6a and the liquid circulation space 38 through the space 351, i.e., the space on the upper side (in FIG. 18) of the urging section 2', permitting a liquid to pass through the interior of the connector 1E.

In addition, since the shape of the space 351 corresponds to the shape of the urging section 2', the urging section 2' is prevented from moving in the housing 3B (the space 351). This ensures that fixation of the urging section 2' in the housing 3B (the space 351) can be omitted.

Figure 9:
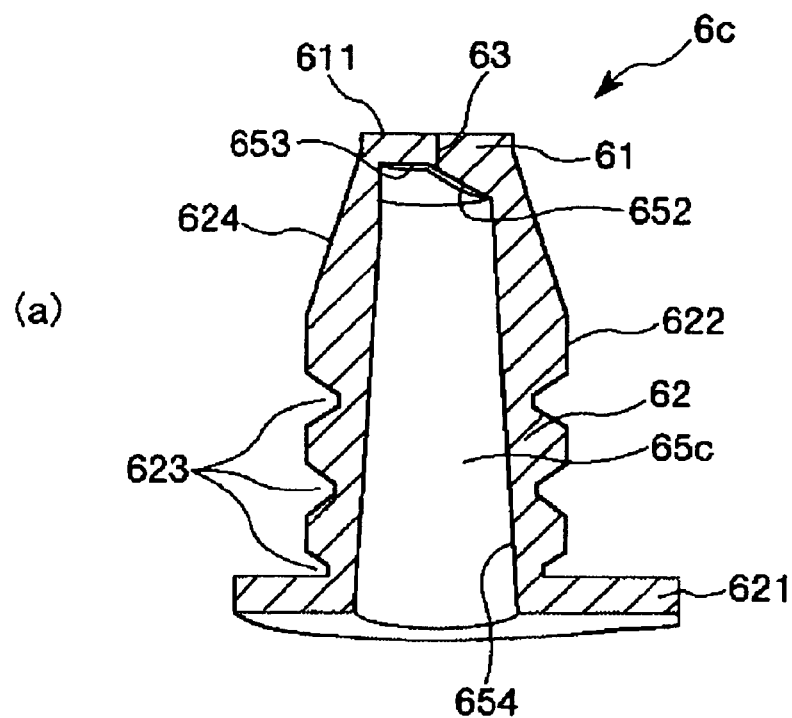
FIG. 9 shows a longitudinal sectional view (a) showing another configuration example of the valve disk, and a perspective view (b) showing another configuration example of the pin.
Figure 9:
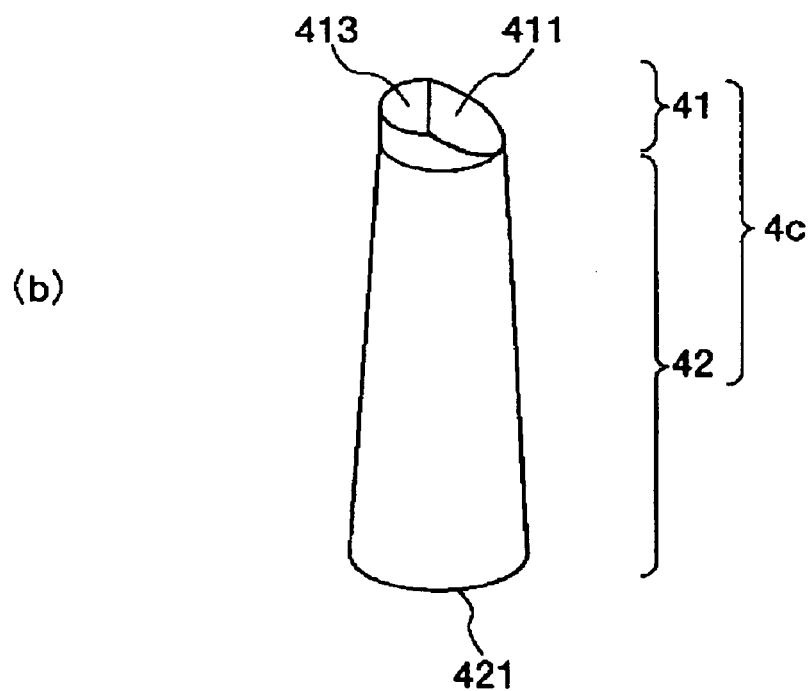
Figure 10:
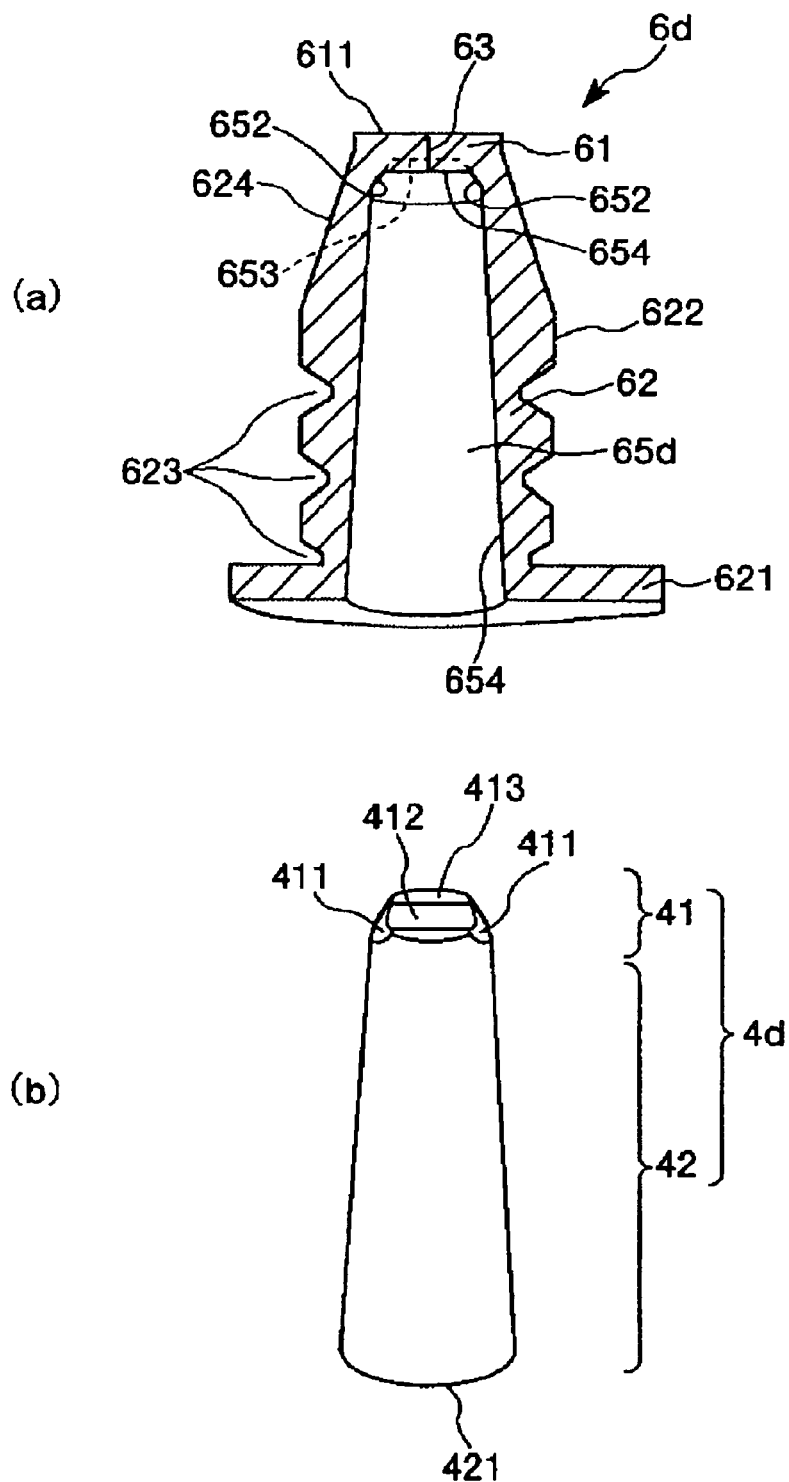
FIG. 10 shows a longitudinal sectional view (a) showing a further configuration example of the valve disk, and a perspective view (b) showing a further example of the pin.

Meanwhile, the first valve disk (the pin insertion space) and the pin are not limited to those shaped as shown in FIGS. 8(a) and 8(b), respectively. Here, other configuration examples of the first valve disk and the pin will be described. FIGS. 9 and 10 each show a longitudinal sectional view (a) showing other configuration example of the valve disk and a perspective view (b) showing other configuration example of the pin. The configuration examples of the first valve disk and the pin will be described below referring to these figures. The following descriptions will be centered on the differences from the first valve disk 6a and the pin 4a above-described, and description of the same items as above will be omitted.

Configuration Example 1

The pin 4c shown in FIG. 9(b) is the same as the pin 4a described above, except for the number of the slant face 411 formed at the top 41 thereof.

The top 41 of the pin 4c is provided with one slant face 411 inclined against the Y-axis direction (the axial direction), and a top face 413. This ensures that, in the connected condition, communication between the passage 101 in the male lure 100 and the clearance 651 (the pin insertion space 65) can be established through the top slit 63.

The first valve disk 6c shown in FIG. 9(a) is the same as the first valve disk 6a described above, except for the shape of a pin insertion space 65c.

This pin insertion space 65c has a shape corresponding to the shape of the pin 4c. Specifically, the pin insertion space 65c is surrounded by a slant face 652 corresponding to the slant face 411, a flat face 653 corresponding to the top face 413, and a tapered surface (inner peripheral surface) 654 corresponding to the tapered part 42. This ensures that, in the non-connected condition, the pin insertion space 65c can be substantially wholly filled up with the pin 4c.

In addition, the slit 63 in the first valve disk 6c is formed at and in parallel to the boundary between the slant face 652 and the flat face 653.

This ensures that, in the connected condition, the clamping force for clamping the portion near the slant face 652 of the top 61 between the slant face 411 and the tip of the male lure 100 is weaker than the clamping force for clamping the portion near the flat face 653 of the top 61 between the top face 413 and the tip of the male lure 100, so that it is easier for the portion near the slant face 652 of the top 61 to be deformed. As a result, the slit 63 can be opened by the pin 4c more assuredly.

Configuration Example 2

The pin 4d shown in FIG. 10(b) is the same as the pin 4a described above, except for the shape of the top 41.

The top 41 of the pin 4d is provided with two slant faces 411 substantially the same as those of the pin 4a, a top face 413, and a recess 412. The recess 412 is formed in the top face 413 so as to range to both the two slant faces 411. Since the top 41 of the pin 4d is shaped in this manner, in the connected condition, communication between the passage 101 in the male lure 100 and the clearance 651 (a pin insertion space 65d) can be established through the top slit 63.

The first valve disk 6d shown in FIG. 10(a) is the same as the first valve disk 6a described above, except for the shape of the pin insertion space 65d.

The pin insertion space 65d has a shape corresponding to the shape of the pin 4d. To be more specific, the pin insertion space 65d is surrounded by a slant face 652 corresponding to the slant face 411, a flat face 653 corresponding to the top face 413, a tapered surface (inner peripheral surface) 654 corresponding to the tapered part 42, and a projected surface 654 corresponding to the recess 412. This ensures that, in the non-connected condition, the pin insertion space 65d can be substantially entirely filled up with the pin 4d. In addition, in the connected condition, the portion near the flat face 653 of the top 61 is clamped between the top face 413 and the tip of the male lure 100, and the pin 4d is moved. Besides, the force with which the portion near the slant face 652 and the projected surface 654 of the top 61 is clamped is weaker, so that the portion is deformed easily. As a result, in the connected condition, the slit 63 can be opened by the pin 4d more easily.

While the connector according to the present invention has been described above referring to the embodiments shown in the drawings, the present invention is not limited to or by these embodiments. The component sections and parts of the connector can be replaced by those of arbitrary configurations which can display the functions the same as or equivalent to the above-mentioned functions. Besides, arbitrary components may be added.

In addition, the pin is not limited to those having lengths approximately equal to the length of the pin insertion space, and the length of the pin may be greater than the length of the pin insertion space.

Besides, the urging sections in the embodiments are not limited to those configured as shown in the figures; for example, the urging section may be composed of a compression coil spring or the like.

In addition, the pin and the urging section may not necessarily be provided as separate members. For example, the pin and the urging section may be formed as one body. This makes it possible to reduce the number of component parts of the connector, and to reduce the number of steps for assembling the connector.

Besides, where the pin and the urging section are formed integrally, the constituent material thereof is not particularly limited; preferably, however, a material having appropriate hardness and restoring ability is adopted. Examples of the constituent material include various rubber materials such as hard silicone rubbers.

In addition, the male-side connecting section is not limited to one which constitutes (forms) a lure taper. For example, the male-side connecting section may be formed to have a male screw like those of the first female-side connecting port and the second female-side connecting port.

INDUSTRIAL APPLICABILITY

The connector according to the present invention includes: a housing having a female-side connecting port to which a tube can be connected, a liquid circulation space through which a liquid is passed, and a tubular male-side connecting section communicating with the liquid circulation space; a valve disk made of elastic material and having a hollow section and a top slit formed in the top and received in the housing; a pin movably installed in the housing, with at least its top inserted in the hollow section; and an urging section for urging the pin axially, wherein the top slit is closed when the tube is not connected to the female-side connecting port; and when the tube is connected to the female-side connecting port, the tube presses the head of the valve disk to contract the valve disk, causing the top slit to spread, communication is thereby established between a tube interior and the hollow section, and at the same time the head of the pin is pressed to cause the pin to move axially, enlarging a clearance between the hollow section and the pin, thereby establishing communication between the tube interior and the male-side connecting section interior successively through the top slit, the hollow section and the liquid circulation space. Therefore, the passage is opened and closed assuredly attendant on the connection and detachment of the tube, so that contamination of the passage can be prevented. In addition, a portion where a liquid stagnates in the interior of the connector can be prevented from being generated. Accordingly, the connector of the present invention has industrial applicability.

The invention claimed is:

1. A connector comprising:
   a housing having a female-side connecting port to which a tube can be connected, a liquid circulation space through which a liquid is passed, and a tubular male-side connecting section communicating with said liquid circulation space;
   a valve disk made of elastic material and having a hollow section and a top slit formed in the top and received in said housing;
   a solid pin movably installed in said housing, with at least its top inserted in said hollow section; and
   an urging section for urging said pin axially, wherein
   said top slit is closed when said tube is not connected to said female-side connecting port; and
   when said tube is connected to said female-side connecting port, said tube presses a head of said valve disk to contract said valve disk, causing said top slit to spread, communication is thereby established between a tube interior and said hollow section, and at the same time the head of said pin is pressed to cause said pin to move axially, enlarging a clearance between said hollow section and said pin, thereby establishing communication between said tube interior and an interior of said male-side connecting section successively through said top slit, said hollow section and said liquid circulation space.

2. The connector as set forth in claim 1, wherein said hollow section is substantially wholly filled up with said pin when said tube is not connected.

3. The connector as set forth in claim 1, wherein two sets of said valve disk, said pin and said urging section which share said liquid circulation space are provided.

4. The connector as set forth in claim 3, wherein said two sets of said valve disk, said pin and said urging section are so arranged that the center lines of said two sets are located in interrelation of skew lines.

5. The connector as set forth in claim 1, wherein said pin has a tapered part gradually decreasing in outside diameter toward the head of said pin.

6. The connector as set forth in claim 1, wherein said pin is provided at the top thereof with a slant face inclined against the axial direction thereof and parallel to the length direction of said top slit.

7. The connector as set forth in claim 1, wherein the top of said pin is so shaped as not to close the mouth of said tube when said tube is connected and the top of said pin abuts on the mouth of said tube.

8. The connector as set forth in claim 6, wherein two said slant faces are provided, and the top of said pin is substantially triangular in longitudinal sectional shape.

9. The connector as set forth in claim 6, wherein said pin is provided with a recess in the head thereof.

10. The connector as set forth in claim 2, wherein two sets of said valve disk, said pin and said urging section which share said liquid circulation space are provided.

11. The connector as set forth in claim 2, wherein said pin has a tapered part gradually decreasing in outside diameter toward the head of said pin.

12. The connector as set forth in claim 2, wherein said pin is provided at the top thereof with a slant face inclined against the axial direction thereof and parallel to the length direction of said top slit.

13. The connector as set forth in claim 12, wherein two said slant faces are provided, and the top of said pin is substantially triangular in longitudinal sectional shape.

14. The connector as set forth in claim 12, wherein said pin is provided with a recess in the head thereof.

15. The connector as set forth in claim 2, wherein the top of said pin is so shaped as not to close the mouth of said tube when said tube is connected and the top of said pin abuts on the mouth of said tube.

16. A connector comprising:
   a housing having a female-side connecting port connectable to a tube and a tubular male-side connecting section possessing a through passage, the housing possessing an interior surface;
   an axially contractable valve disk of elastic material surrounding a hollow section of the valve disk, the valve disk being positioned in the housing, the valve disk possessing a top in which is formed a slit, the slit being closed when the tube is not connected to the female-side connecting port, the valve disk possessing an interior surface;
   a pin having a top end portion positioned in the hollow section of the valve disk, the pin possessing an outer surface and being movable relative to the housing and the valve disk;
   an urging section which urges the pin axially toward the top of the valve disk, the urging section possessing an outer surface;
   a liquid circulation space located between the inner surface of the housing and the outer surface of the urging section, the liquid circulation space being in fluid communication with the through passage of the male-side connecting section so that liquid in the liquid circulation space flows into the passage of the male-side connecting section;
   the valve disk axially contracting to enlarge a space between the interior surface of the valve disk and the outer surface of the top end portion of the pin, and the pin moving relative to the housing and the valve disk, when the tube is connected to the female-side connecting port to cause the top of the pin to extend through the slit and change the slit from a closed state to an open state, thereby establishing communication between an interior of the tube and the through passage of the male-side connecting section successively through the slit, the space between the interior surface of the valve disk and the outer surface of the top end portion of the pin, and the liquid circulation space; and
   the pin being devoid of a hollow section through which liquid passes when the tube is connected to the female-side connecting port.

17. The connector as set forth in claim 16, wherein the top of the pin is provided with a recess.

18. The connector as set forth in claim 16, wherein the pin comprises a top end portion possessing a tapering outer configuration that gradually tapers toward the top of the pin.

* * * * *